US 12,089,649 B2

(12) United States Patent
Yamada et al.

(10) Patent No.: US 12,089,649 B2
(45) Date of Patent: Sep. 17, 2024

(54) AEROSOL GENERATION APPARATUS, AND METHOD AND NON-TRANSITORY COMPUTER-READABLE STORAGE MEDIUM STORING PROGRAM FOR OPERATING SAME

(71) Applicant: JAPAN TOBACCO INC., Tokyo (JP)

(72) Inventors: Manabu Yamada, Tokyo (JP); Takeshi Akao, Tokyo (JP); Kazuma Mizuguchi, Tokyo (JP); Hajime Fujita, Tokyo (JP)

(73) Assignee: JAPAN TOBACCO INC., Tokyo (JP)

(*) Notice: Subject to any disclaimer, the term of this patent is extended or adjusted under 35 U.S.C. 154(b) by 1036 days.

(21) Appl. No.: 17/023,406

(22) Filed: Sep. 17, 2020

(65) Prior Publication Data
US 2021/0022405 A1 Jan. 28, 2021

Related U.S. Application Data

(63) Continuation of application No. PCT/JP2018/011665, filed on Mar. 23, 2018.

(51) Int. Cl.
A24F 40/50 (2020.01)
A24F 40/51 (2020.01)
(Continued)

(52) U.S. Cl.
CPC .............. A24F 40/50 (2020.01); A24F 40/51 (2020.01); A24F 40/53 (2020.01); A24F 40/10 (2020.01); A61M 11/00 (2013.01); A61M 15/06 (2013.01)

(58) Field of Classification Search
CPC .......... A24F 40/50; A24F 40/53; A24F 40/51; A24F 40/10; A61M 11/00; A61M 15/06
(Continued)

(56) References Cited

U.S. PATENT DOCUMENTS 9,609,895 B2 * 4/2017 Galloway ............... A24F 40/50
9,913,497 B2 * 3/2018 Galloway ............... A24F 40/80
(Continued)

FOREIGN PATENT DOCUMENTS

EP 2 654 469 6/2012
EP 3 086 671 7/2015
(Continued)

OTHER PUBLICATIONS

Extended European Search Report issued Mar. 16, 2021 in European Application No. 18910638.8.
(Continued)

Primary Examiner — Abdullah A Riyami
Assistant Examiner — Vladimir Imas
(74) Attorney, Agent, or Firm — XSENSUS LLP

(57) ABSTRACT

There is provided an aerosol generation apparatus capable of determining whether an aerosol source is insufficient in quantity while suppressing variation in a generation quantity of aerosol in a period during which a user inhales aerosol. An aerosol generation apparatus comprises a power supply 110, a storage section that stores an aerosol source or an aerosol base material that retains the aerosol source, a load 132 that atomizes the aerosol source using heat generated by electric power from the power supply 110 and in which an electric resistance value changes depending on a temperature, a first sensor 112B, 112D that outputs a value related to the electric resistance value of the load 132, a second sensor that generates an output upon receipt of a user's request with regard to an aerosol generation, a first circuit 202 that is connected in series between the power supply 110 and the load 132, and includes a first switch Q1, a second circuit 204 that is connected in parallel to the first circuit 202, includes a second switch Q2, and has an electric resistance value higher than an electric resistance value of the first circuit
(Continued)

202, and a control section 106 that controls the first switch Q1 and the second switch Q2, in which the control section 106 is configured to estimate a residual quantity of the aerosol source based on the value output by the first sensor 112B, 112D when the second switch Q2 is in an on state, and to control so that a period during which the output is generated by the second sensor includes a time point at which the second switch Q2 become an on state when the first switch Q1 is in an on state or a time point at which the second switch Q2 turns an on state and the first switch Q1 turns an off state.

17 Claims, 15 Drawing Sheets

(51) Int. Cl.
    *A24F 40/53*     (2020.01)
    *A24F 40/10*     (2020.01)
    *A61M 11/00*     (2006.01)
    *A61M 15/06*     (2006.01)

(58) Field of Classification Search
    USPC .......................................................... 131/329
    See application file for complete search history.

(56) References Cited

U.S. PATENT DOCUMENTS

| | | | |
|---|---|---|---|
| 9,949,507 B2* | 4/2018 | Flick | A24F 40/50 |
| 10,321,711 B2* | 6/2019 | Henry, Jr. | A24F 40/65 |
| 10,368,581 B2* | 8/2019 | Rostami | H04L 65/1069 |
| 10,772,355 B2* | 9/2020 | Zuber | A61M 11/042 |
| 10,813,385 B2* | 10/2020 | Sur | A24B 15/167 |
| 10,881,144 B2* | 1/2021 | Batista | A61M 15/06 |
| 10,925,315 B2* | 2/2021 | Bilat | A24F 40/40 |
| 10,959,459 B2* | 3/2021 | Sur | H05B 1/0227 |
| 10,966,460 B2* | 4/2021 | Frisbee | A61M 15/06 |
| 11,134,721 B2* | 10/2021 | Marubashi | H02J 7/0063 |
| 11,627,763 B2* | 4/2023 | Yamada | A24F 40/53 131/329 |
| 2013/0306084 A1* | 11/2013 | Flick | B63C 9/115 131/328 |
| 2013/0319435 A1* | 12/2013 | Flick | A61M 11/041 219/490 |
| 2015/0208729 A1 | 7/2015 | Monsees et al. | |
| 2017/0238610 A1* | 8/2017 | Reevell | G06F 1/04 |
| 2018/0070641 A1* | 3/2018 | Batista | A24F 40/50 |
| 2020/0237010 A1* | 7/2020 | Yamada | H05B 1/0244 |
| 2020/0352246 A1* | 11/2020 | Yamada | A24F 40/42 |

FOREIGN PATENT DOCUMENTS

| | | | | |
|---|---|---|---|---|
| EP | 3487326 A1 * | 5/2019 | | A24B 15/167 |
| EP | 3769634 A1 * | 1/2021 | | A24F 40/50 |
| JP | 2017-501805 A | 1/2017 | | |
| WO | 2016/150922 A2 | 9/2016 | | |
| WO | 2017/084818 A1 | 5/2017 | | |
| WO | 2017/144191 A1 | 8/2017 | | |

OTHER PUBLICATIONS

International Search Report and Written Opinion mailed on May 22, 2018, 2018 for PCT/JP2018/011665 filed on Mar. 23, 2018, 6 pages including English Translation of the International Search Report.

* cited by examiner

AEROSOL GENERATION APPARATUS, AND METHOD AND NON-TRANSITORY COMPUTER-READABLE STORAGE MEDIUM STORING PROGRAM FOR OPERATING SAME

CROSS REFERENCE TO RELATED APPLICATIONS

This application is a Continuation of PCT International Application No. PCT/JP2018/011665, filed on Mar. 23, 2018, which is hereby expressly incorporated by reference into the present application.

TECHNICAL FIELD

The present disclosure relates to an aerosol generation apparatus that generates aerosol to be inhaled by a user, and a method and a program for operating the same.

BACKGROUND ART

In an aerosol generation apparatus such as a general electronic cigarette, a heated cigarette, or nebulizer, the aerosol generation apparatus being configured to generate aerosol to be inhaled by a user, if the user performs inhalation when an aerosol source to be atomized to generate the aerosol is insufficient in quantity, a sufficient quantity of aerosol cannot be supplied to the user. In addition, in the case of the electronic cigarette or the heated cigarette, there may be a problem in that the aerosol having an intended inhaling flavor cannot be generated.

As a solution to this problem, PTL 1 discloses a technique for measuring a heater temperature after an elapse of a predetermined time period since a completion of an aerosol generation phase to determine a liquid level in a liquid storage section. PTL 2 discloses a technique for measuring an electric parameter of a heater in a period of inactivity of the heater and detecting liquid depletion based on an amount of electric power supplied to the heater obtained from the measured result and a resulting changes in temperature of the heater.

However, in the conventional techniques, since the liquid level or the liquid depletion can be detected only in the period of inactivity of the heater, an opportunity for determining whether an aerosol source is insufficient in quantity is limited.

CITATION LIST

Patent Literature

PTL 1: International Publication No. WO 2017/144191
PTL 2: International Publication No. WO 2017-084818

SUMMARY OF INVENTION

Technical Problem

The present disclosure has been devised in view of the point described above.

A problem to be solved by the present disclosure is to provide an aerosol generation apparatus capable of determining whether an aerosol source is insufficient in quantity in a period during which a user inhales aerosol, and a method and a program for operating the same.

Solution to Problem

In order to solve the problem described above, according to an embodiment of the present disclosure, there is provided an aerosol generation apparatus, comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, wherein the control section is configured to: estimate a residual quantity of the aerosol source based on the value output by the first sensor when the second switch is in an on state; and control so that a period during which the output is generated by the second sensor includes: a time point at which the second switch turns an on state when the first switch is in an on state, or a time point at which the second switch turns an on state at the same time as the first switch becoming an off state.

In an embodiment, the control section is configured to: cause the second switch to be an on state after the first switch turns an on state; and simultaneously transmit an off signal to the first switch and an on signal to the second switch.

In an embodiment, the control section is configured to: cause the first switch to be an on state after the second switch turns an on state; and simultaneously transmit an on signal to the first switch and an off signal to the second switch.

In an embodiment, the control section is configured to transmit, when one of the first switch and the second switch is in an on state, an on signal to the other of the first switch and the second switch.

In an embodiment, the control section is configured to: maintain anon state of the first switch for a predetermined time period; and transmit an on signal to the second switch before an elapse of a time period since an on signal is transmitted to the first switch or the first switch turns an on state, the time period being obtained by subtracting, from the predetermined time period, a turn-on time period of the second switch.

In an embodiment, the control section is configured to transmit an off signal to the one of the first switch and the second switch after an on signal is transmitted to the other of the first switch and the second switch.

In an embodiment, the control section is configured to transmit, during a turn-off period of one of the first switch and the second switch, an on signal to the other of the first switch and the second switch.

In an embodiment, the control section is configured to transmit, during a turn-on period of one of the first switch and the second switch, an off signal to the other of the first switch and the second switch.

In an embodiment, the control section is configured to estimate a residual quantity of the aerosol source based on the value output by the first sensor after an off signal is transmitted to the first switch.

In an embodiment, the control section is configured to estimate a residual quantity of the aerosol source based on the value output by the first sensor after an elapse of a turn-off time period of the first switch since transmission of an off signal to the first switch.

In an embodiment, the control section is configured to cause the first switch to be always in an on state and the second switch to be intermittently in an on state while the output is generated by the second sensor.

In an embodiment, the control section is configured to cause a time period during which the first switch is in an on state to be longer than a time period during which the second switch is in an on state while the output is generated by the second sensor.

In an embodiment, the aerosol generation apparatus comprises a voltage converter that is connected between the power supply and a node, the node connected to a higher voltage side of the first circuit and a higher voltage side of the second circuit, wherein the control section is configured to control the voltage converter to output a constant voltage while the second switch is in an on state.

In an embodiment, the first switch and the second switch are comprised of any of switches having the same characteristics, transistors having the same characteristics, and contactors having the same characteristics.

In an embodiment, the second sensor detects a flow rate or a flow velocity generated by a user's inhalation through the aerosol generation apparatus, and generates the output only while the flow rate or the flow velocity exceeds a first threshold and does not fall below a second threshold.

In an embodiment, the second sensor detects a change in a pressure generated by a user's inhalation through the aerosol generation apparatus, and generates the output only while the pressure falls below a first threshold and does not exceed a second threshold.

In an embodiment, a period during which a switch is in an on state is a period from when a current flowing through the switch becomes higher than a predetermined value until the current decreases to the predetermined value, and a period during which a switch is in an off state is a period during which the switch is not in an on state.

According to the embodiment of the present disclosure, there is provided a method of operating an aerosol generation apparatus, the aerosol generation apparatus comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, the method comprising the steps of, by the control section: estimating a residual quantity of the aerosol source based on the value output by the first sensor when the second switch is in an on state; and controlling so that a period during which the output is generated by the second sensor includes: a time point at which the second switch turns an on state when the first switch is in an on state, or a time point at which the second switch turns an on state at the same time as the first switch becoming an off state.

In addition, according to the embodiment of the present disclosure, there is provided an aerosol generation apparatus, comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, wherein the control section is configured to: estimate a residual quantity of the aerosol source based on the value output by the first sensor when the second switch is in an on state; and control the first switch and the second switch so that a power supply by the power supply continues while the output is generated by the second sensor.

In addition, according to the embodiment of the present disclosure, there is provided a method of operating an aerosol generation apparatus, the aerosol generation apparatus comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, the method comprising the steps of, by the control section: estimating a residual quantity of the aerosol source based on the value output by the first sensor when the second switch is in an on state; and controlling the first switch and the second switch so that a power supply by the power supply continues while the output is generated by the second sensor.

In addition, according to the embodiment of the present disclosure, there is provided an aerosol generation apparatus, comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, wherein the control section is configured to estimate a residual quantity of the aerosol source based on the value output by the first sensor when the second switch is in an on state, when the output is generated by the second sensor, and when an aerosol is generated by the load or immediately after generation of an aerosol by the load is stopped.

In addition, according to the embodiment of the present disclosure, there is provided a method of operating an aerosol generation apparatus, the aerosol generation apparatus comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, the method comprising the step of, by the control section, estimating a residual quantity of the aerosol source based on the value output by the first sensor when the second switch is in an on state, when the output is generated by the second sensor, and when an aerosol is generated by the load or immediately after generation of an aerosol by the load is stopped.

In addition, according to the embodiment of the present disclosure, there is provided an aerosol generation apparatus, comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, wherein the control section is configured to: estimate a residual quantity of the aerosol source based on the value output by the first sensor when the second switch is in an on state; and transmit an on signal to the second switch in a period, the period is that during which the output is generated by the second sensor, is included in a period during which the first switch is in an on state, and ends before a time period from a time point at which a period during which the first switch is in an on state ends, the time period is from when an on signal is transmitted to the second switch until the second switch turns an on state.

In addition, according to the embodiment of the present disclosure, there is provided a method of operating an aerosol generation apparatus, the aerosol generation apparatus comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, the method comprising the steps of, by the control section: estimating a residual quantity of the aerosol source based on the value output by the first sensor when the second switch is in an on state; and transmitting an on signal to the second switch in a period, the period is that during which the output is generated by the second sensor, is included in a period during which the first switch is in an on state, and ends before a time period from a time point at which a period during which the first switch is in an on state ends, the time period is from when an on signal is transmitted to the second switch until the second switch turns an on state.

In addition, according to the embodiment of the present disclosure, there is provided an aerosol generation apparatus, comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, wherein the control section is configured to: estimate a residual quantity of the aerosol source based on the value output by the first sensor when the second switch is in an on state; and transmit an on signal to the second switch when transmitting an off signal to the first switch while the output is generated by the second sensor, and wherein a turn-off time period of the first switch is equal to or longer than a time period from when an on signal is transmitted to the second switch until the second switch turns an on state.

In addition, according to the embodiment of the present disclosure, there is provided a method of operating an aerosol generation apparatus, the aerosol generation apparatus comprising: a storage section that stores an aerosol source or an aerosol base material that retains the aerosol source; a first sensor that outputs a value related to an electric resistance value of a load, which its electric resistance value changes depending on a temperature of the load, which atomizes the aerosol source using heat generated by electric power from a power supply; a second sensor that generates an output upon receipt of a user's request with regard to an aerosol generation; a first circuit that is connected in series between the power supply and the load, and includes a first switch; a second circuit that is connected in parallel to the first circuit, includes a second switch, and has an electric resistance value higher than an electric resistance value of the first circuit; and a control section that controls the first switch and the second switch, the method comprising the steps of, by the control section: estimating a residual quantity of the aerosol source based on the value output by the first sensor when the second switch is in an on state; and transmitting an on signal to the second switch when transmitting an off signal to the first switch while an output is generated by the second sensor, wherein a turn-off time period of the first switch is equal to or longer than a time period from when an on signal is transmitted to the second switch until the second switch turns an on state.

In addition, according to the embodiment of the present disclosure, there is provided a program, when being executed by a processor, causes the processor to perform the above method.

Advantageous Effects of Invention

According to the embodiment of the present disclosure, there can be provided an aerosol generation apparatus capable of determining whether an aerosol source is insufficient in quantity in a period during which a user inhales aerosol, and a method and a program for operating the same.

DESCRIPTION OF EMBODIMENTS

Hereinafter, embodiments of the present disclosure will be described in detail with reference to the drawings. Note that the embodiments of the present disclosure include an electronic cigarette, a heated cigarette, and a nebulizer, but are not limited to the electronic cigarette, the heated cigarette, and the nebulizer. The embodiments of the present disclosure can include various aerosol generation apparatuses for generating aerosol to be inhaled by a user.

Figure 1A:
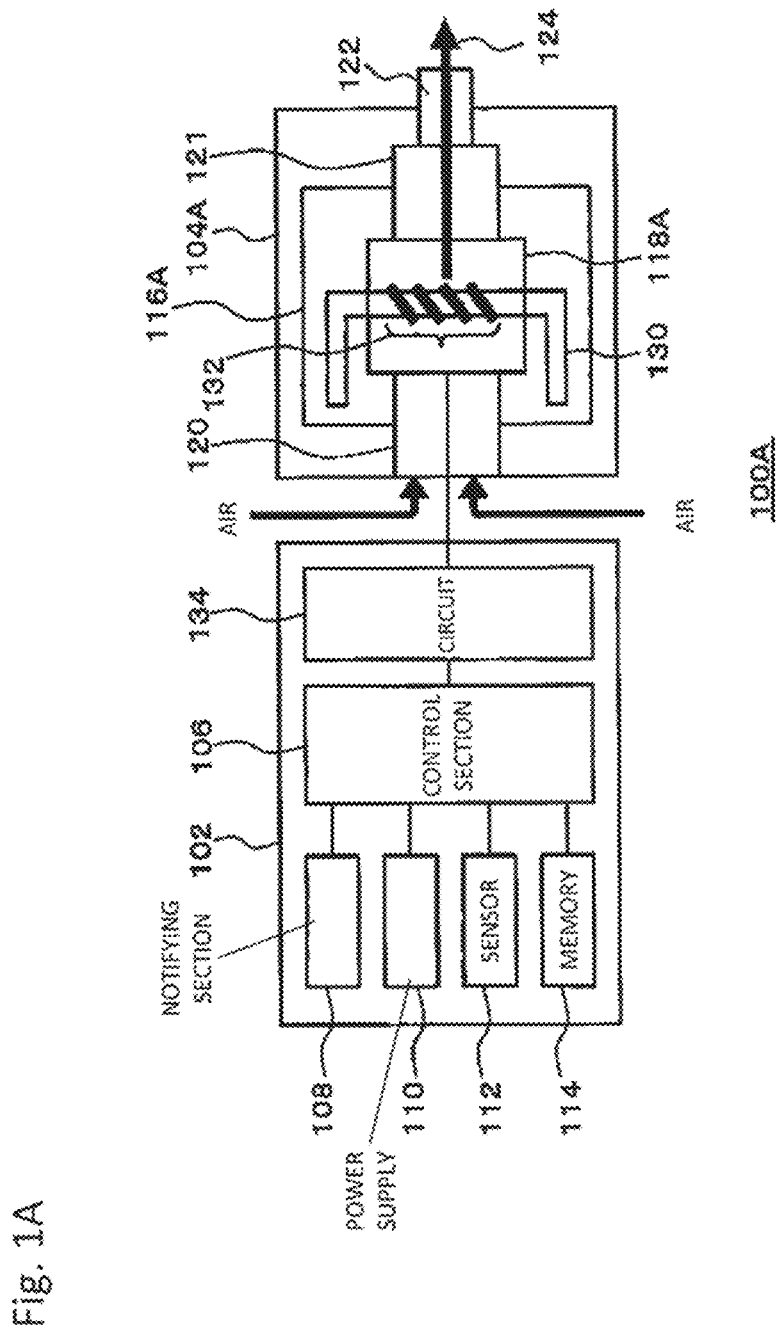
FIG. 1A is a schematic block diagram of a configuration of an aerosol generation apparatus according to an embodiment of the present disclosure.

FIG. 1A is a schematic block diagram of a configuration of an aerosol generation apparatus 100A according to an embodiment of the present disclosure. It should be noted that FIG. 1A schematically and conceptually illustrates components included in the aerosol generation apparatus 100A and does not illustrate strict disposition, shapes, dimensions, positional relations, and the like of the components and the aerosol generation apparatus 100A.

As illustrated in FIG. 1A, the aerosol generation apparatus 100A includes a first member 102 (hereinafter, referred to as a "main body 102") and a second member 104A (hereinafter, referred to as a "cartridge 104A"). As illustrated in the figure, as an example, the main body 102 may include a control section 106, a notifying section 108, a power supply 110, a sensor 112, and a memory 114. The aerosol generation apparatus 100A may include sensors such as a flow sensor, a pressure sensor, and a voltage sensor, and these sensors are collectively referred to as the "sensor 112" in the present disclosure. The main body 102 may also include a circuit 134 described later. As an example, the cartridge 104A may include a storage section 116A, an atomizing section 118A, an air intake channel 120, an aerosol flow path 121, a mouthpiece section 122, a retention section 130, and a load 132. Some of the components included in the main body 102 may be included in the cartridge 104A. Some of the components included in the cartridge 104A may be included in the main body 102. The cartridge 104A may be configured to be detachably attached to the main body 102. Alternatively, all the components included in the main body 102 and the cartridge 104A may be included in the same housing instead of the main body 102 and the cartridge 104A.

The storage section 116A may be configured as a tank that stores an aerosol source. In this case, the aerosol source is liquid, for example, polyalcohol such as glycerin or propylene glycol, or water. When the aerosol generation apparatus 100A is an electronic cigarette, the aerosol source in the storage section 116A may include a tobacco raw material that emits an inhaling flavor component by being heated or an extract deriving from the tobacco raw material. The retention section 130 retains the aerosol source. For example, the retention section 130 is formed of a fibrous or porous material, and retains the aerosol source, which is liquid, in gaps among fibers or thin holes of a porous material. For example, cotton, glass fiber, a tobacco raw material or the like can be used as the above-mentioned fibrous or porous material. When the aerosol generation apparatus 100A is a medical inhaler such as a nebulizer, the aerosol source may also include a drug to be inhaled by a patient. As another example, the storage section 116A may have a configuration in which a consumed aerosol source can be replenished. Alternatively, the storage section 116A itself may be configured to be replaceable when the aerosol source is consumed. The aerosol source is not limited to liquid, and may be solid. When the aerosol source is solid, the storage section 116A may be a hollow container.

The atomizing section 118A is configured to atomize the aerosol source and generate aerosol. When an inhaling operation is detected by the sensor 112, the atomizing section 118A generates the aerosol. For example, the retention section 130 is provided to couple the storage section 116A and the atomizing section 118A. In this case, a part of the retention section 130 communicates with the inside of the storage section 116A and is in contact with the aerosol source. Another part of the retention section 130 extends to the atomizing section 118A. Note that the other part of the retention section 130 extending to the atomizing section 118A may be accommodated in the atomizing section 118A, or may communicate with the inside of the storage section 116A again through the atomizing section 118A. The aerosol source is carried from the storage section 116A to the atomizing section 118A by a capillary effect of the retention section 130. As an example, the atomizing section 118A includes a heater including the load 132 that is electrically connected to the power supply 110. The heater is disposed in contact with or in close contact with the retention section 130. When an inhaling operation is detected, the control section 106 controls the heater of the atomizing section 118A, and heats the aerosol source carried through the retention section 130 to thereby atomize the aerosol source. Another example of the atomizing section 118A may be an ultrasonic atomizer that atomizes the aerosol source by ultrasonic vibration. The air intake channel 120 is connected to the atomizing section 118A, and communicates with the outside of the aerosol generation apparatus 100A. The aerosol generated in the atomizing section 118A is mixed with air taken in via the air intake channel 120. Mixed fluid of the aerosol and the air is delivered to the aerosol flow path 121 as indicated by an arrow 124. The aerosol flow path 121 has a tubular structure for transporting, to the mouthpiece section 122, the mixed fluid of the aerosol generated in the atomizing section 118A and the air.

The mouthpiece section 122 is located at a terminal end of the aerosol flow path 121, and is configured to open the aerosol flow path 121 to the outside of the aerosol generation apparatus 100A. The user holds the mouthpiece section 122 in the user's mouth and performs the inhalation to thereby take the air containing the aerosol in the user's mouth.

The notifying section 108 may include a light emitting element such as an LED, a display, a speaker, a vibrator, or the like. The notifying section 108 is configured to perform some notification to the user with light emission, display, sound production, vibration, or the like according to necessity.

The power supply 110 supplies electric power to the components such as the notifying section 108, the sensor 112, the memory 114, the load 132, and the circuit 134 of the aerosol generation apparatus 110A. The power supply 110 may be a primary battery or a secondary battery that can be charged by being connected to an external power supply via a predetermined port (not illustrated) of the aerosol generation apparatus 100A. Only the power supply 110 may be detachable from the main body 102 or the aerosol generation apparatus 100A, or may be replaceable with a new power supply 110. The power supply 110 may be replaceable with a new power supply 110 by replacing the entire main body 102 with a new main body 102.

The sensor 112 may include one or more sensors that are used to acquire a value of a voltage applied to all or a specific portion in the circuit 134, a value related to a resistance value of the load 132, a value related to a temperature of the load 132, or the like. The sensor 112 may be incorporated in the circuit 134. The function of the sensor 112 may be incorporated in the control section 106. The sensor 112 may also include the pressure sensor that detects fluctuation in pressure in the air intake channel 120 and/or the aerosol flow path 121 or the flow sensor that detects a flow rate in the air intake channel 120 and/or the aerosol flow path 121. The sensor 112 may also include a weight sensor that detects a weight of a component such as the storage section 116A. The sensor 112 may be also configured to count the number of times that the user puffs using the aerosol generation apparatus 100A. The sensor 112 may be also configured to integrate an energization time to the atomizing section 118A. The sensor 112 may be also configured to detect a height of a liquid surface in the storage section 116A. The sensor 112 may be also configured to obtain or detect an SOC (State of Charge), a current integrated value, a voltage and the like of the power supply 110. The SOC may be obtained by a current integration method (coulomb counting method), an SOC-OCV (Open Circuit Voltage) method, or the like. The sensor 112 may be also an operation button or the like that is operable by the user.

The control section 106 may be an electronic circuit module configured as a microprocessor or a microcomputer. The control section 106 may be also configured to control the operation of the aerosol generation apparatus 100A according to computer executable instructions stored in the memory 114. The memory 114 is a storage medium such as a ROM, a RAM, or a flash memory. In the memory 114, in addition to the above-mentioned computer executable instructions, setting data required for controlling the aerosol generation apparatus 100A and the like may be stored. For example, the memory 114 may store various pieces of data such as a control method of the notifying section 108 (aspects, etc. of light emission, sound production, vibration, etc.), a value acquired and/or detected by the sensor 112, and a heating history of the atomizing section 118A. The control section 106 reads the data from the memory 114 according to necessity to use it for control of the aerosol generation apparatus 100A, and stores the data in the memory 114 according to necessity.

Figure 1B:
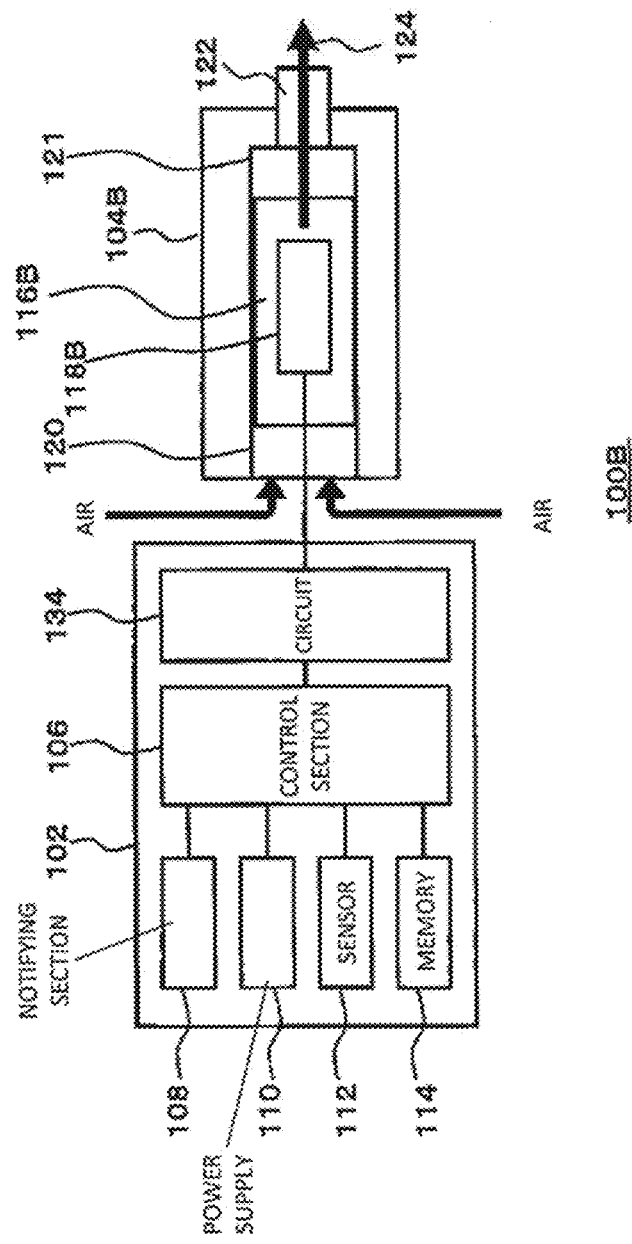
FIG. 1B is a schematic block diagram of a configuration of an aerosol generation apparatus according to an embodiment of the present disclosure.

FIG. 1B is a schematic block diagram of a configuration of an aerosol generation apparatus 100B according to an embodiment of the present disclosure.

As illustrated in the figure, the aerosol generation apparatus 100B has a configuration similar to that of the aerosol generation apparatus 100A of FIG. 1A. Note that a configuration of a second member 104B (hereinafter, referred to as an "aerosol generating article 104B" or a "stick 104B") is different from that of the first member 104A. As an example, the aerosol generating article 104B may include an aerosol base material 116B, an atomizing section 118B, an air intake channel 120, an aerosol flow path 121, and a mouthpiece section 122. Some of the components included in the main body 102 may be included in the aerosol generating article 104B. Some of the components included in the aerosol generating article 104B may be included in the main body 102. The aerosol generating article 104B may be configured to be insertable/extractable into/from the main body 102.

Alternatively, all the components included in the main body 102 and the aerosol generating article 104B may be included in the same housing instead of the main body 102 and the aerosol generating article 104B.

The aerosol base material 116B may be configured as a solid carrying the aerosol source. As in the case of the storage section 116A in FIG. 1A, the aerosol source may be liquid, for example, polyalcohol such as glycerin or propylene glycol, or water. The aerosol source in the aerosol base material 116B may include a tobacco raw material that emits an inhaling flavor component by being heated or an extract deriving from the tobacco raw material. When the aerosol generation apparatus 100A is a medical inhaler such as a nebulizer, the aerosol source may also include a drug to be inhaled by a patient. The aerosol base material 116B itself may be configured to be replaceable when the aerosol source is consumed. The aerosol source is not limited to liquid, and may be a solid.

The atomizing section 118B is configured to atomize the aerosol source and generate aerosol. When an inhaling operation is detected by the sensor 112, the atomizing section 118B generates the aerosol. The atomizing section 118B includes a heater (not illustrated) including a load that is electrically connected to the power supply 110. When an inhaling operation is detected, the control section 106 controls the heater of the atomizing section 118B, and heats the aerosol source carried in the aerosol base material 116B to thereby atomize the aerosol source. Another example of the atomizing section 118B may be an ultrasonic atomizer that atomizes the aerosol source by ultrasonic vibration. The air intake channel 120 is connected to the atomizing section 118B, and communicates with the outside of the aerosol generation apparatus 100B. The aerosol generated in the atomizing section 118B is mixed with air taken in via the air intake channel 120. Mixed fluid of the aerosol and the air is delivered to the aerosol flow path 121 as indicated by an arrow 124. The aerosol flow path 121 has a tubular structure for transporting, to the mouthpiece section 122, the mixed fluid of the aerosol generated in the atomizing section 118B and the air.

The control section 106 is configured to control the aerosol generation apparatuses 100A and 100 (hereinafter also generically referred to as an "aerosol generation apparatus 100") according to the embodiment of the present disclosure in various methods.

In the aerosol generation apparatus, if the user performs the inhalation when the aerosol source is insufficient in quantity, a sufficient quantity of aerosol cannot be supplied to the user. In addition, in the case of the electronic cigarette or the heated cigarette, the aerosol having an unintended inhaling flavor may be emitted (hereinafter, such a phenomenon is also referred to as "unintended behavior"). The unintended behavior may occur not only when the aerosol source in the storage section 116A or the aerosol base material 116B is insufficient in quantity, but also when a sufficient quantity of aerosol source remains in the storage section 116A but the aerosol source in the retention section 130 is temporarily insufficient in quantity. The present inventors have invented an aerosol generation apparatus that performs an appropriate control when an aerosol source is insufficient in quantity, and a method and a program for operating the same. Hereinafter, each embodiment of the present disclosure will be described in detail, while mainly assuming the case where the aerosol generation apparatus has a configuration illustrated in FIG. 1A. However, the case where the aerosol generation apparatus has a configuration illustrated in FIG. 1B is also described according to necessity. It will be apparent to those skilled in the art that the embodiment of the present disclosure is also applicable to the case where the aerosol generation apparatus has various configurations other than those illustrated in FIG. 1A and FIG. 1B.

Figure 2:
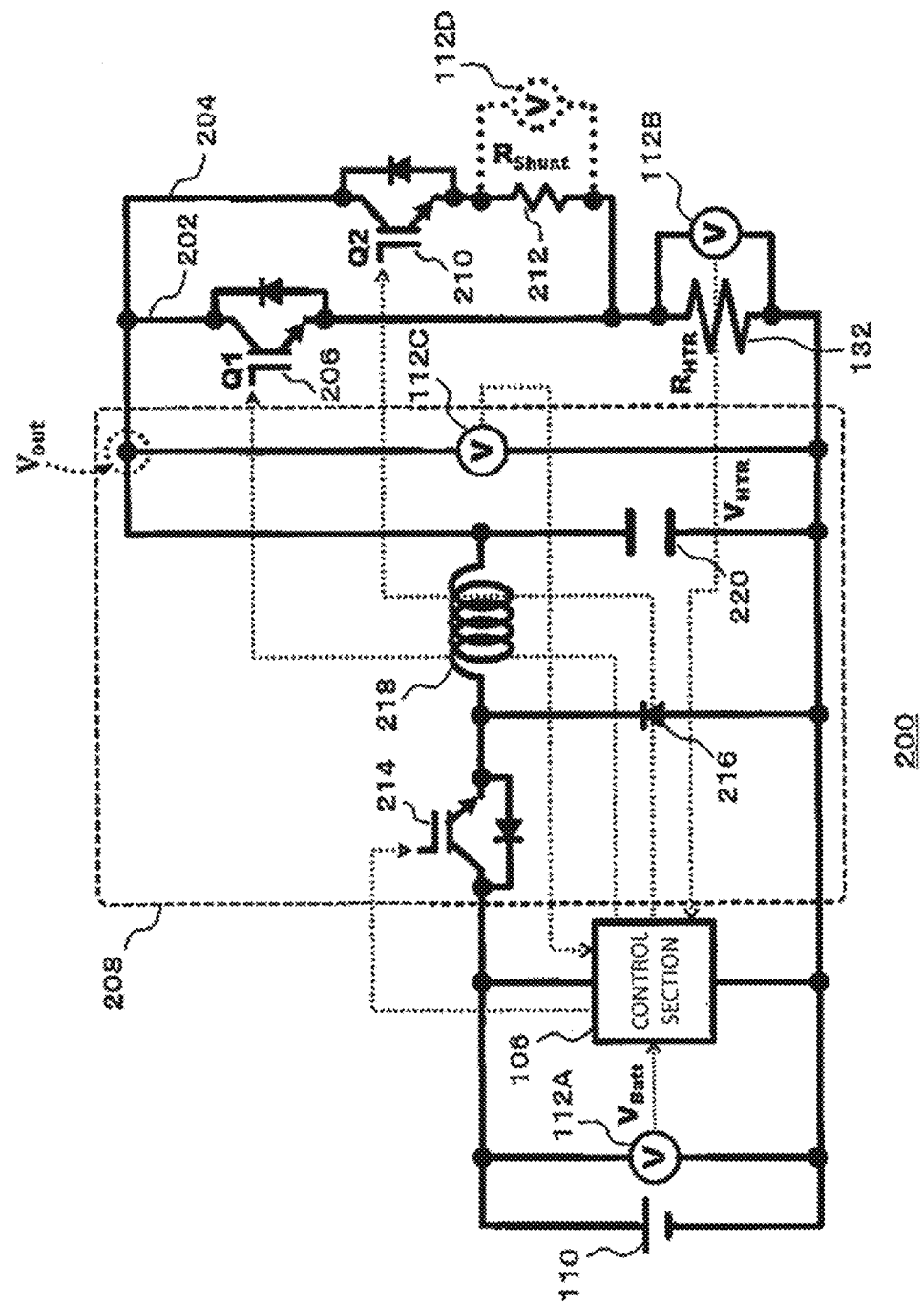
FIG. 2 is a diagram illustrating an exemplary circuit configuration of a portion of an aerosol generation apparatus according to an embodiment of the present disclosure.

FIG. 2 is a diagram illustrating an exemplary circuit configuration of a portion of the aerosol generation apparatus 100A according to a first embodiment of the present disclosure.

A circuit 200 illustrated in FIG. 2 includes the power supply 110, the control section 106, the sensors 112A to 112D (hereinafter also collectively referred to as the "sensor 112"), the load 132 (hereinafter also referred to as a "heater resistor"), a first circuit 202, a second circuit 204, a switch Q1 including a first field effect transistor (FET) 206, a conversion section 208, a switch Q2 including a second FET 210, and a resistor 212 (hereinafter, also referred to as a "shunt resistor"). The electric resistance value of the load 132 changes in response to a temperature. The shunt resistor 212 is connected in series with the load 132, and has a known electric resistance value. The electric resistance value of the shunt resistor 212 may be invariant to the temperature. The shunt resistor 212 has an electric resistance value larger than that of the load 132. Depending on the embodiment, the sensors 112C and 112D may be omitted. It will be apparent to those skilled in the art that not only FET but also various elements such as IGBT and a contactor can be used as the switches Q1 and Q2. It is preferable that the switches Q1 and Q2 have the same characteristics. Accordingly, it is preferable that the FET, the IGBT, the contactor, and the like that are used as the switches Q1 and Q2 have the same characteristics. This is because the processing described below can be easily implemented by providing the switches Q1 and Q2 having the same characteristics.

The conversion section 208 may be, for example, a switching converter, and may include a FET 214, a diode 216, an inductor 218, and a capacitor 220. The control section 106 may control the conversion section 208 so that the conversion section 208 converts an output voltage of the power supply 110 to apply the converted output voltage to the entire circuit. Here, it is preferable that the conversion section 208 is configured to output a constant voltage under the control of the control section 106 at least while the switch Q2 is in an on state (described later). In addition, under the control of the control section 106, the conversion section 208 may be configured to output a constant voltage also while the switch Q1 is in an on state or always. Note that the constant voltage output by the conversion section 208 under the control of the control section 106 while the switch Q1 is in an on state may be the same as or different from the constant voltage output by the conversion section 208 under the control of the control section 106 while the switch Q2 is in an on state. If these constant voltages are different from each other, the constant voltage output by the conversion section 208 under the control of the control section 106 while the switch Q1 is in an on state may be higher or lower than the constant voltage output by the conversion section 208 under the control of the control section 106 while the switch Q2 is in an on state. According to the above configuration, since a voltage and a parameter when the voltage is measured (described later) are stabilized, the estimation accuracy of a residual quantity of the aerosol is improved. Furthermore, the conversion section 208 may be configured to, under the control of the control section 106, directly apply an output voltage of the power supply 110 to the first circuit while the switch Q1 is in an on state.

Note that the conversion section 208 is not an essential component, and can be omitted.

The circuit 134 illustrated in FIG. 1A may be electrically connected to the power supply 110 and the load 132, and may include the first circuit 202 and the second circuit 204. The first circuit 202 and the second circuit 204 are connected in parallel to the power supply 110 and the load 132. The first circuit 202 may include the switch Q1. The second circuit 204 may include the switch Q2 and the resistor 212 (and optionally the sensor 112D). The first circuit 202 may have a resistance value lower than that of the second circuit 204. In this example, the sensors 112B and 112D are voltage sensors, and are configured to detect a potential difference (hereinafter, also referred to as a "voltage" or a "voltage value") across the load 132 and a potential difference (hereinafter, also referred to as a "voltage" or a "voltage value") across the resistor 212, respectively. However, a configuration of the sensor 112 is not limited thereto. For example, the sensor 112 may be also a current sensor, and may detect a value of a current flowing through the load 132 and/or the resistor 212.

As indicated by dotted-line arrows in FIG. 2, the control section 106 can control the switch Q1, the switch Q2, and the like, and can acquire a value detected by the sensor 112. The control section 106 may be configured to switch the switch Q1 from an off state to an on state to cause the first circuit 202 to function and configured to switch the switch Q2 from an off state to an on state to cause the second circuit 204 to function. The control section 106 may be configured to alternately switch the switches Q1 and Q2 to alternately cause the first circuit 202 and the second circuit 204 to function.

The first circuit 202 is used to atomize the aerosol source. When the switch Q1 is switched to an on state to cause the first circuit 202 to function, the electric power is supplied to the heater (or the load 132 in the heater), and the load 132 is heated. The aerosol source retained in the retention section 130 in the atomizing section 118A (in the case of the aerosol generation apparatus 100 of FIG. 1B, the aerosol source carried in the aerosol base material 116B) is atomized through heating of the load 132, whereby the aerosol is generated.

The second circuit 204 is used to acquire a value of a voltage applied to the load 132, a value related to a resistance value of the load 132, a value of a voltage applied to the resistor 212, and the like. As an example, it is assumed that the sensors 112B and 112D included in the second circuit 204 are voltage sensors as illustrated in FIG. 2. When the switch Q2 is on and the second circuit 204 is functioning, the current flows through the switch Q2, the resistor 212, and the load 132. A value of the voltage applied to the load 132 and a value of the voltage applied to the resistor 212 is obtained by the sensors 112B and 112D, respectively. In addition, a value of a current flowing through the load 132 can be obtained using the value of the voltage applied to the resistor 212 that has been acquired by the sensor 112D and a known resistance value $R_{shunt}$ of the resistor 212. Since a total value of the resistance values of the resistor 212 and the load 132 can be obtained based on an output voltage $V_{out}$ of the conversion section 208 and the obtained current value, a resistance value $R_{HTR}$ of the load 132 can be obtained by subtracting the known resistance value $R_{shunt}$ from the total value. When the load 132 has a positive or negative temperature coefficient characteristic in which the resistance value changes in response to the temperature, the temperature of the load 132 can be estimated based on a relationship between the pre-known resistance value of the load 132 and the temperature of the load 132, and the resistance value $R_{HTR}$ of the load 132 that is obtained as described above. It will be appreciated by those skilled in the art that the resistance value and the temperature of the load 132 can be estimated using a value of the current flowing through the resistor 212. The value related to the resistance value of the load 132 in this example may include a voltage value, a current value and the like of the load 132. A specific example of the sensors 112B and 112D is not limited to the voltage sensor, and may include the other elements such as a current sensor (for example, a hall element).

The sensor 112A detects an output voltage of the power supply 110. The sensor 112C detects an output voltage of the conversion section 208. Alternatively, the output voltage of the conversion section 208 may be a predetermined target voltage. These voltages are voltages applied to the entire circuit.

The resistance value $R_{HTR}$ of the load 132 when the temperature of the load 132 is "$T_{HTR}$" can be expressed as follows.

$$R_{HTR}(T_{HTR}) = (V_{HTR} \times R_{shunt})/(V_{Batt} - V_{HTR}) \quad (1)$$

Here, "$V_{Batt}$" is a voltage applied to the entire circuit. When the conversion section 208 is not used, "$V_{Batt}$" is an output voltage of the power supply 110. When the conversion section 208 is used, "$V_{Batt}$" corresponds to the output voltage $V_{out}$ of the conversion section 208 or the target voltage of the conversion section 208. "$V_{HTR}$" is a voltage applied to the heater. Instead of "$V_{HTR}$," the voltage applied to the shunt resistor 212 may be used.

Figure 3:
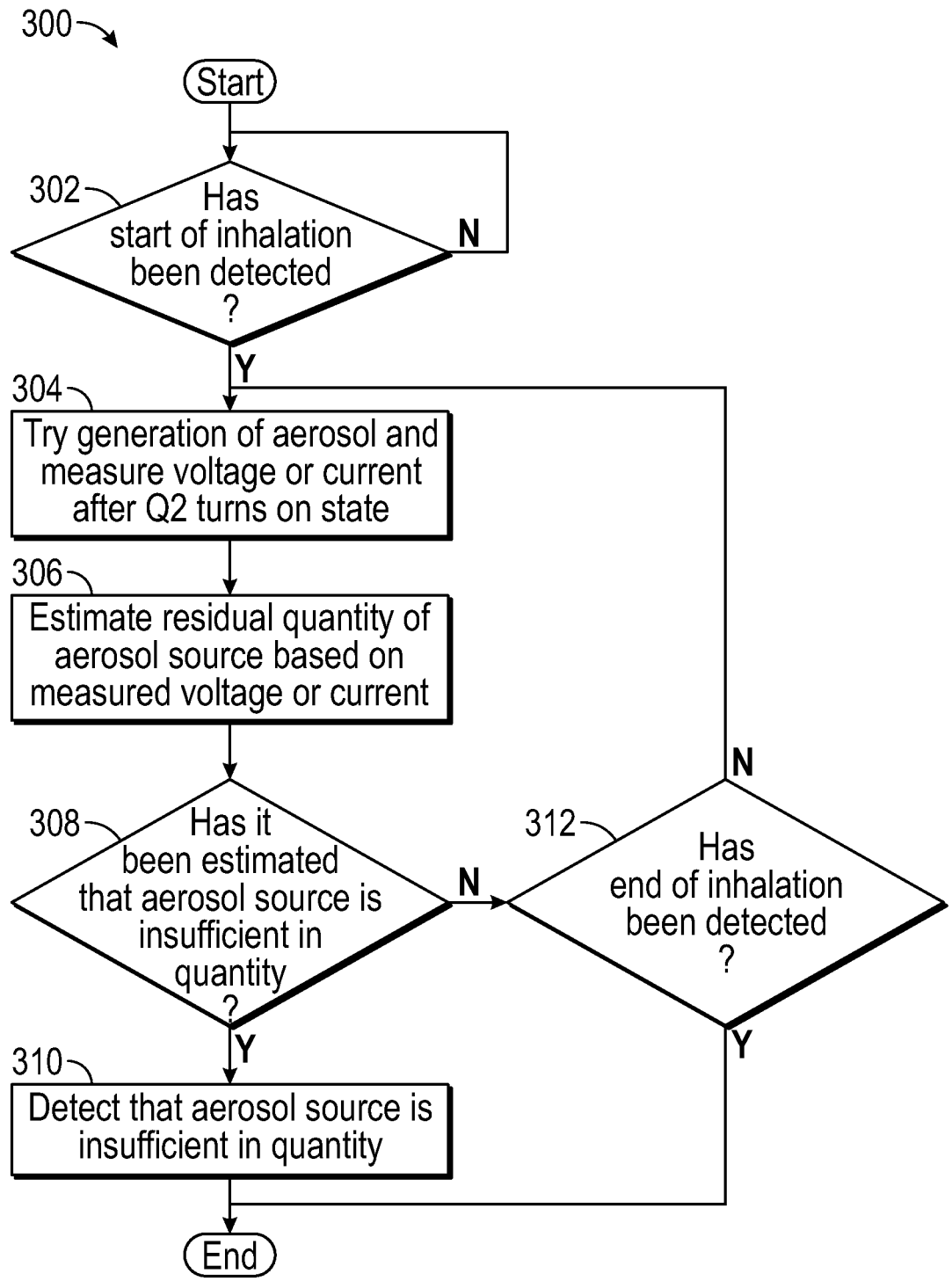
FIG. 3 is a flowchart of exemplary processing of determining whether an aerosol source is insufficient in quantity, according to an embodiment of the present disclosure.

FIG. 3 is a flowchart of exemplary processing 300 of determining whether the aerosol source is insufficient in quantity, according to an embodiment of the present disclosure. Here, all the steps will be described as being performed by the control section 106. However, it should be noted that some of the steps may be performed by another component in the aerosol generation apparatus 100.

The process starts at step 302. In step 302, the control section 106 determines whether the start of a user's inhalation has been detected, based on the information obtained from the pressure sensor, the flow sensor, and the like. For example, when an output value i.e., a pressure of the pressure sensor falls below a predetermined threshold, the control section 106 can determine that the start of the user's inhalation has been detected. In addition, for example, when an output value i.e., a flow rate or a flow velocity of the flow sensor exceeds a predetermined threshold, the control section 106 can determine that the start of the user's inhalation has been detected. In such a determination method, the aerosol can be generated according to the feeling of the user, and therefore the flow sensor is particularly preferable. Alternatively, when the output values of these sensors start to continuously change, the control section 106 may determine that the start of the user's inhalation has been detected. Alternatively, the control section 106 may determine that the start of the user's inhalation has been detected, based on a fact that a button for starting the generation of the aerosol has been pressed, etc.

When the start of the inhalation is not detected ("N" in step 302), the process of step 302 is repeated.

When it is determined that the start of the inhalation has been detected ("Y" in step 302), the process proceeds to step 304. In step 304, the control section 106 tries generation of the aerosol, and measures the voltage or the current after the switch Q2 turns an on state.

Figure 4:
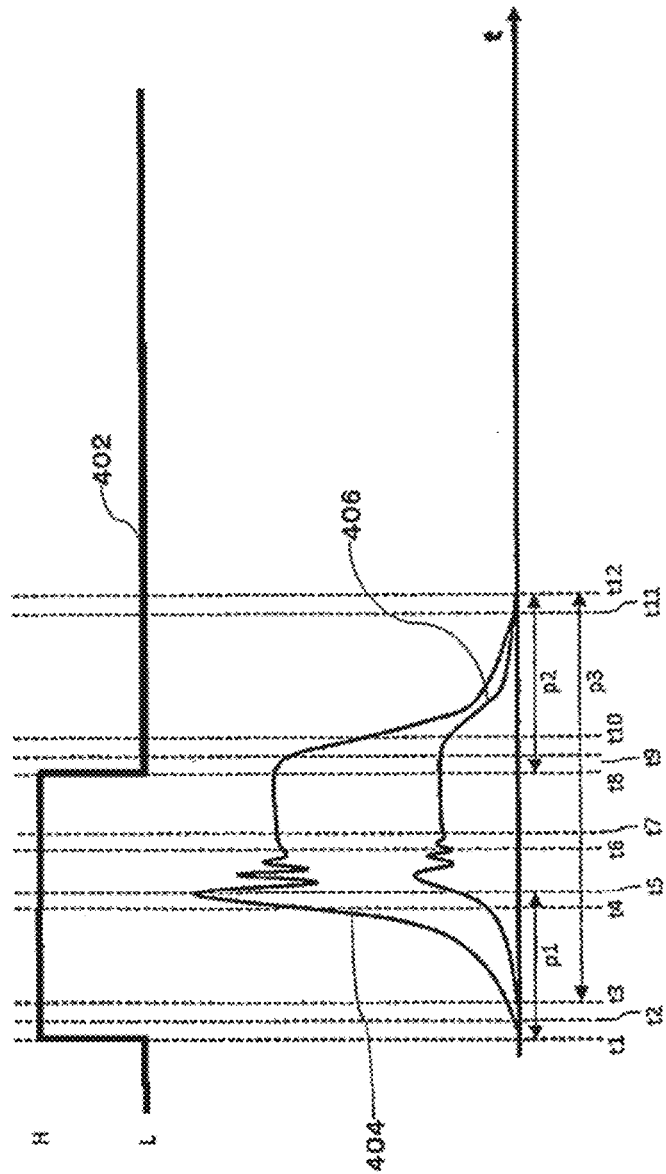
FIG. 4 is a graph for illustrating terms regarding the switch, according to an embodiment of the present disclosure.

Here, a fact that the switch is in the "on state" and the other terms regarding the switch will be described with reference to FIG. 4 using the switch Q1 or Q2 of FIG. 2 as an example.

Reference numeral 402 shows an example of a change over time t in a signal S ("L" or "H") transmitted to the switch Q1 or Q2 from the control section 106. Reference numeral 404 shows an example of a change over a time t in a gate-source voltage $V_{GS}$ of the first FET 206 or the second FET 210. Reference numeral 406 shows an example of a changeover the time t in a current $I_{DS}$ flowing between a drain and a source of the first FET 206 or the second FET. It should be noted that the changes in a signal and the like shown in FIG. 4 are merely exemplary, and the magnitude relationship among the examples in the vertical direction, timings of various time points, and the like are not limited to those shown in FIG. 4.

"t1" represents a time point at which the signal S transitions from L (low) to H (high). "t2" represents a time point at which the voltage $V_{GS}$ exceeds a predetermined threshold (hereinafter, referred to as a "first threshold") of zero or more, and "t3" represents a time point at which the current $I_{DS}$ exceeds a predetermined threshold (hereinafter, referred to as a "second threshold") of zero or more. "t4" represents a time point at which the voltage $V_{GS}$ exceeds a predetermined threshold (hereinafter, referred to as a "third threshold") for the first time after the time t2, and "t5" represents a time point at which the current $I_{DS}$ exceeds a predetermined threshold (hereinafter, referred to as a "fourth threshold") for the first time after the time t3. "t6" represents a time point at which a voltage surge or a transient voltage fluctuation of the voltage $V_{GS}$ is settled, and "t7" represents a time point at which a current surge or a transient current fluctuation of the current $I_{DS}$ is settled. "t8" represents a time point at which the signal S transitions from H to L. "t9" represents a time point at which the voltage $V_{GS}$ falls below a predetermined threshold (hereinafter, referred to as a "fifth threshold") after the time t6, and "t10" represents a time point at which the current $I_{DS}$ falls below a predetermined threshold (hereinafter, referred to as a "sixth threshold") after the time t7. Note that the fifth threshold and the sixth threshold may be the same as or different from the third threshold and the fourth threshold, respectively. "t11" represents a time point at which the voltage $V_{GS}$ decreases to a predetermined threshold (hereinafter, referred to as a "seventh threshold") of zero or more, and "t12" represents a time point at which the current $I_{DS}$ decreases to a predetermined threshold (hereinafter, referred to as an "eighth threshold") of zero or more. Note that the seventh threshold and the eighth threshold may be the same as or different from the first threshold and the second threshold, respectively.

In the present embodiment, an "on signal" and an "off signal" are defined to be transmitted to the switch at the time t1 and the time t8, respectively.

In the present embodiment, a "turn-on period" of the switch is defined as a period p1 that starts at the time t1 and ends at the time t5. In another embodiment, a "turn-on period" may be defined as a period that ends at another time point including the times t4, t6, and t7. Note that a length of the "turn-on period" is referred to as a "turn-on time period". In addition, in the present embodiment, a "turn-off period" of the switch is defined as a period p2 that starts at the time t8 and ends at the time t12. In another embodiment, a "turn-off period" may be defined as a period that ends at another time point including the time t11. Note that a length of the "turn-off period" is referred to as a "turn-off time period".

In the present embodiment, a period during which the switch is in the "on state" is defined as a period p3 that starts at the time t3 and ends at the time t12. In another embodiment, a period during which the switch is in the "on state" may be defined as a period that starts at another time point including the time t2. In addition, in another embodiment, a period during which the switch is in the "on state" may be defined as a period that ends at another time point including the time t11. Furthermore, a period during which the switch is in the "off state" is defined as a period during which the switch is not in the "on state".

Returning to FIG. 3, in the present embodiment, the voltage or current measured in step 304 is a voltage $V_{HTR}$ applied to the load 132. In another embodiment, the voltage or current measured in step 304 may be the current $I_{HTR}$ flowing through the load 132, or the voltage $V_{shunt}$ applied to the shunt resistor 212 or the current $I_{shunt}$ flowing through the shunt resistor. In the case where the control section 106 measures the voltage or current of one of the load 132 and the shunt resistor 212, this step may include a step of calculating the voltage or current of the other. Note that more specific processes included in step 304 will be described later.

The process proceeds to step 306. In step 306, the control section 106 estimates a residual quantity of the aerosol source based on the voltage or current measured in step 304. Subsequently, the process proceeds to step 308. In step 308, the control section 106 determines whether to estimate that the aerosol source is insufficient in quantity. Here, the principle for estimating that the aerosol source is insufficient in quantity will be described with reference to FIG. 5.

When the heater is operating, the supply quantity of the aerosol source is balanced with the generation quantity of the aerosol if the aerosol source is sufficiently supplied from the storage section 116A, whereby the retention section 130 retains a certain quantity of the aerosol source. However, at least if the aerosol source in the storage section 116A is insufficient in quantity, the supply quantity becomes insufficient, whereby the quantity of the aerosol source retained in the retention section 130 gradually decreases.

Figure 5:
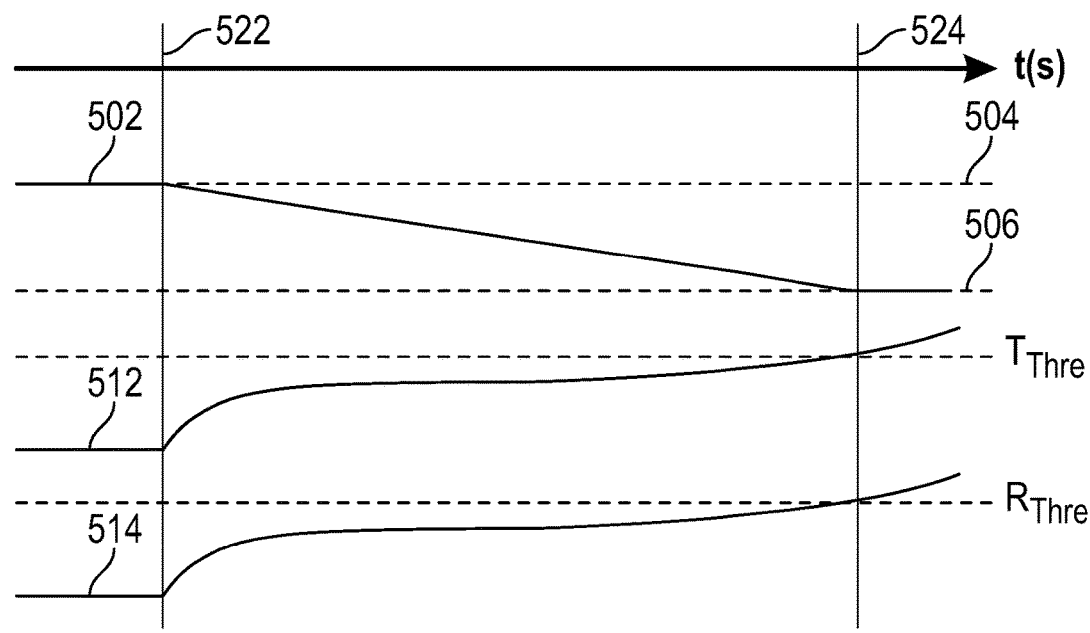
FIG. 5 is a graph for showing a principle to determine whether an aerosol source is insufficient in quantity, according to an embodiment of the present disclosure.
Figure 6A:
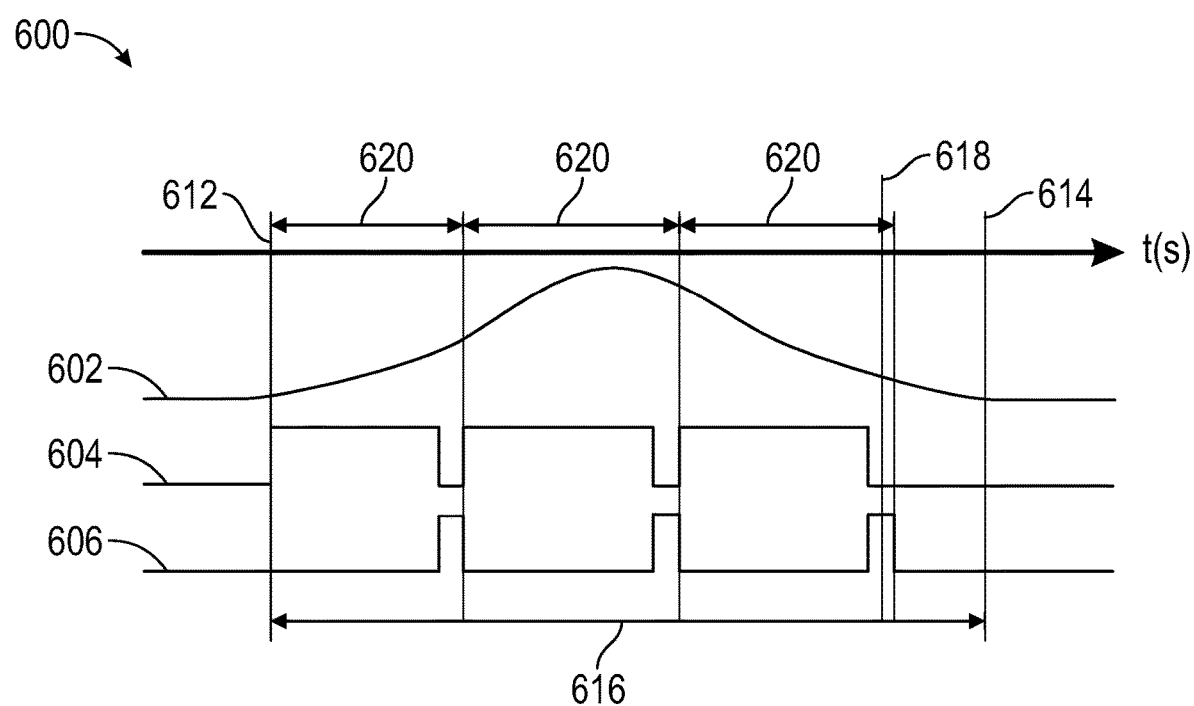
FIG. 6A is a graph showing an example of changes over time in an output value of a sensor and signals according to exemplary processing of determining whether an aerosol source is insufficient in quantity.
Figure 6B:
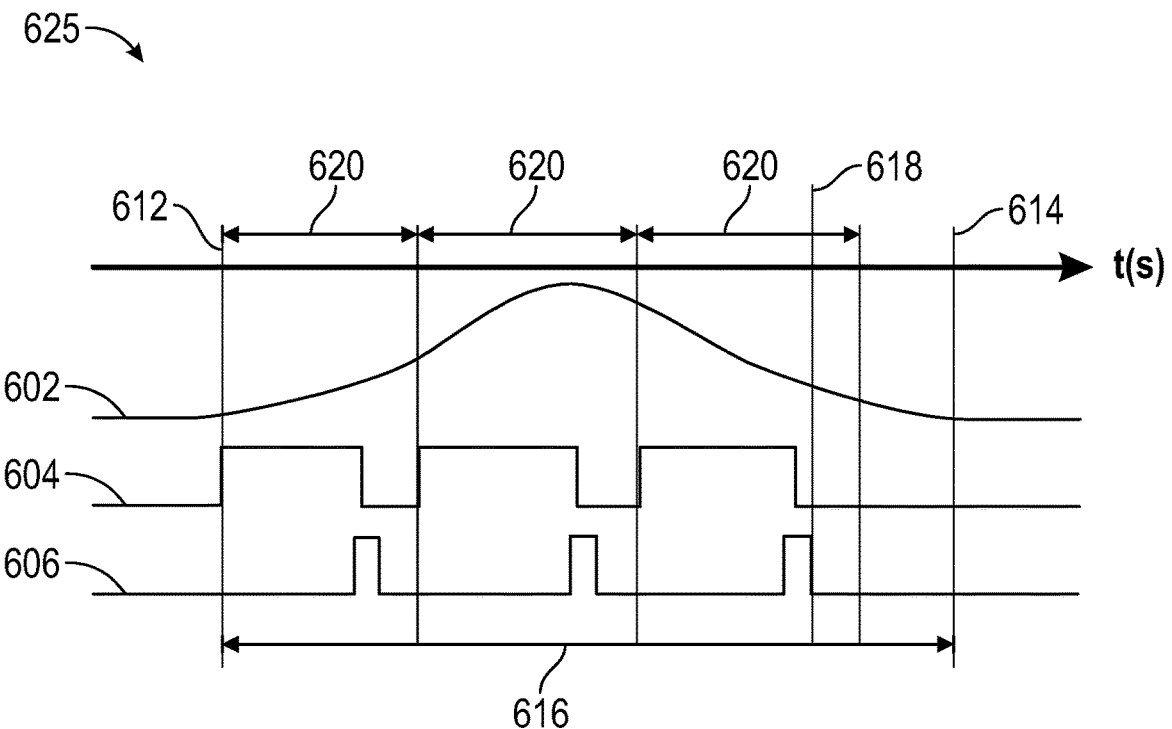
FIG. 6B is a graph showing an example of changes over time in an output value of a sensor and signals according to exemplary processing of determining whether an aerosol source is insufficient in quantity.
Figure 6C:
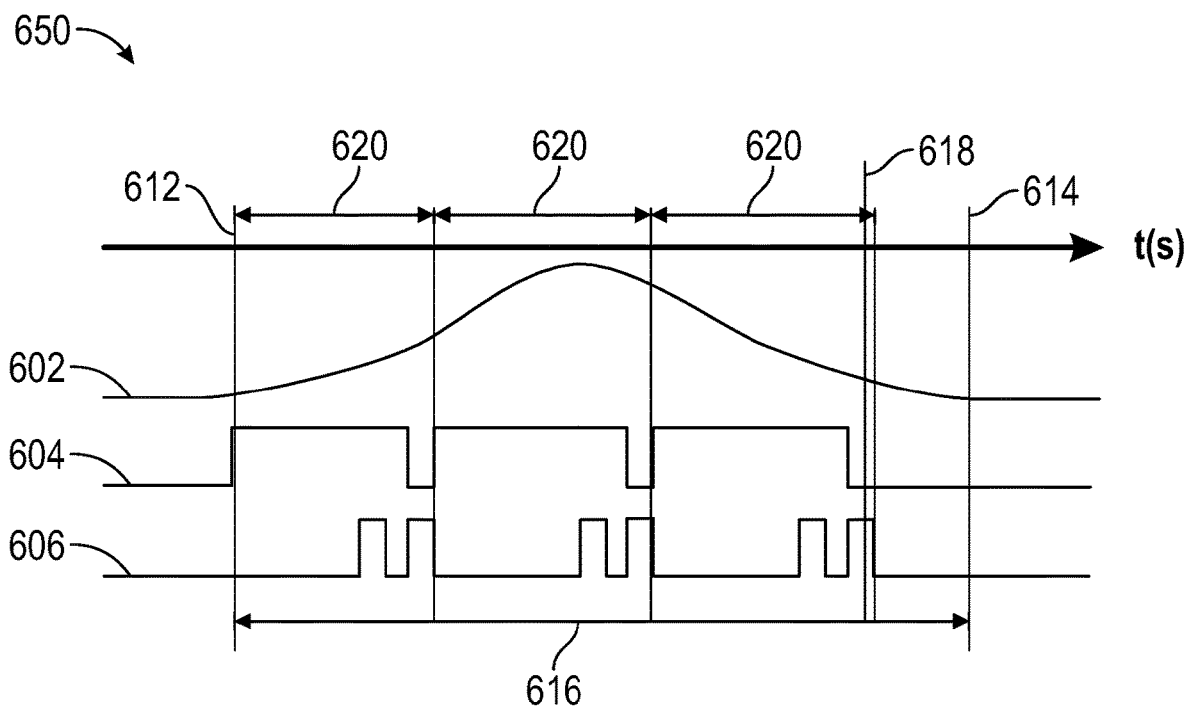
FIG. 6C is a graph showing an example of changes over time in an output value of a sensor and signals according to exemplary processing of determining whether an aerosol source is insufficient in quantity.
Figure 6D:
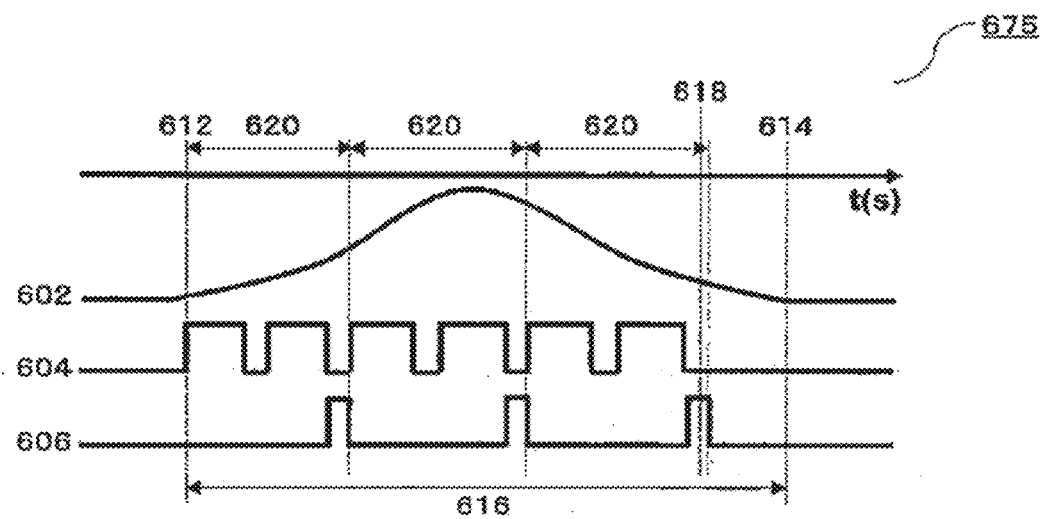
FIG. 6D is a graph showing an example of changes over time in an output value of a sensor and signals according to exemplary processing of determining whether an aerosol source is insufficient in quantity.

FIG. 5 shows an example of a change over time in each physical quantity, when the heater is operating. Reference numeral 502 shows an example of a change over a time t in a quantity of the aerosol source retained in the retention section 130. Reference numeral 504 shows a quantity of the aerosol source retained in the retention section 130 when the aerosol source in the storage section 116A is not insufficient in quantity, and reference numeral 506 indicates zero. Reference numerals 512 and 514 show examples of changes over the time t in the temperature $T_{HTR}$ of the load 132 and the resistance value $R_{HTR}$ of the load 132, respectively. As described above, when the load 132 has a positive or negative temperature coefficient characteristic, the examples of changes over the time t in the temperature $T_{HTR}$ of the load 132 and the resistance value $R_{HTR}$ of the load 132 are similar to each other.

FIG. 5 shows that when the quantity of the aerosol source retained in the retention section 130 starts to decrease at a time 522, the temperature $T_{HTR}$ of the load 132 also starts to increase therewith, and accordingly the resistance value $R_{HTR}$ of the load 132 also starts to increase. In other words, the time 522 represents a time point at which the temperature $T_{HTR}$ or the resistance value $R_{HTR}$ starts to increase.

Here, when the temperature $T_{HTR}$ or the resistance value $R_{HTR}$ of the load 132 at a time 524 when the quantity of the aerosol source retained in the retention section 130 becomes zero is obtained in advance as a threshold $T_{Thre}$ or $R_{Thre}$, the threshold $T_{Thre}$ or $R_{Thre}$ can be used to determine whether the temperature $T_{HTR}$ or the resistance value $R_{HTR}$ of the load 132 that is calculated based on the measured voltage or current is higher than or equal to or higher than the threshold $T_{Thre}$ or $R_{Thre}$, which makes it possible to estimate whether the aerosol source is insufficient in quantity. Note that the threshold $T_{Thre}$ or $R_{Thre}$ need not be exactly the same as the temperature $T_{HTR}$ or the resistance value $R_{HTR}$ at the time 524, and may be the temperature $T_{HTR}$ or the resistance value $R_{HTR}$ at a predetermined time point after the time 522, i.e., the time point when the temperature $T_{HTR}$ or the resistance value $R_{HTR}$ starts to increase. Note that an example of the threshold $T_{Thre}$ is 300° C. to 400° C.

In the circuit illustrated in FIG. 2, when the switch Q1 is in an off state and the switch Q2 is in an on state, a relationship between the resistance value $R_{HTR}$ and the voltage $V_{HTR}$ of the load 132 is expressed by the above-described expression (1). The expression (1) represents that the resistance value $R_{HTR}$ is a function of the voltage $V_{HTR}$ of the load 132, and the resistance value $R_{HTR}$ increases as the voltage $V_{HTR}$ increases. Accordingly, when the voltage $V_{HTR}$ of the load 132 at a predetermined time point including the time 524 after the time 522 is obtained in advance as a threshold, the threshold can be used to determine whether the voltage $V_{HTR}$ is higher than or equal to or higher than the threshold, which makes it possible to estimate whether the aerosol source is insufficient in quantity.

A relationship between the resistance value $R_{HTR}$ of the load 132 and the current $I_{HTR}$ flowing through the load 132 (=a current flowing through the shunt resistor 212) is expressed as follows.

$$R_{HTR} = V_{BATT}/I_{HTR} - R_{shunt} \quad (2)$$

The expression (2) represents that the resistance value $R_{HTR}$ is a function of the current $I_{HTR}$, and the resistance value $R_{HTR}$ increases as the current $I_{HTR}$ decreases. Accordingly, when the current $I_{HTR}$ at a predetermined time point including the time 524 after the time 522 is obtained in advance as a threshold, the threshold can be used to determine whether the current $I_{HTR}$ is lower than or equal to or lower than the threshold, which makes it possible to estimate whether the aerosol source is insufficient in quantity.

Furthermore, a relationship between the resistance value $R_{HTR}$ of the load 132 and the voltage $V_{shunt}$ applied to the shunt resistor 212 is expressed as follows.

$$R_{HTR} = \{(V_{Batt} - V_{shunt})/V_{shunt}\} \times R_{shunt} \quad (3)$$

The expression (3) represents that the resistance value $R_{HTR}$ is a function of the voltage $V_{shunt}$, and the resistance value $R_{HTR}$ increases as the voltage $V_{shunt}$ decreases. Accordingly, when the voltage $V_{shunt}$ at a predetermined time point including the time 524 after the time 522 is obtained in advance as a threshold, the threshold can be used to determine whether the voltage $V_{shunt}$ is lower than or equal to or lower than the threshold, which makes it possible to estimate whether the aerosol source is insufficient in quantity.

Note that it will be appreciated that even when both of the switches Q1 and Q2 are in an on state, the control section 106 can estimate, by a similar principle to that described above, whether the residual quantity of the aerosol source is insufficient, in consideration of a substantial resistance value of the first circuit 202 excluding the load 132.

Accordingly, returning to FIG. 3, step 308 may include a step of determining whether the value of the current or voltage measured in step 304 is lower than, higher than, equal to or lower than, or equal to or higher than the predetermined threshold. In addition, step 306 may include a step of calculating the resistance value $R_{HTR}$ of the load 132, and step 308 may include a step of determining whether the resistance value $R_{HTR}$ is higher than or equal to or higher than the threshold $R_{T}re$. Furthermore, step 306 may include a step of calculating the temperature $T_{HTR}$ of the load 132, and step 308 may include a step of determining whether the temperature $T_{HTR}$ is higher than or equal to or higher than the threshold $T_{Thre}$.

When the aerosol source is estimated to be insufficient in quantity ("Y" in step 308), the process proceeds to step 310. In step 310, the control section 106 detects that the aerosol source is insufficient in quantity, and performs a desired process.

When it is not estimated that the aerosol source is insufficient in quantity ("N" in step 308), the process proceeds to step 312. In step 312, the control section 106 determines whether the end of the user's inhalation has been detected, based on the information obtained from the pressure sensor, the flow sensor and the like. For example, when an output value i.e., a pressure of the pressure sensor exceeds a predetermined threshold, the control section 106 can determine that the end of the user's inhalation has been detected. In addition, for example, when an output value i.e., a flow rate or a flow velocity of the flow sensor falls below a predetermined threshold which may be zero, the control section 106 can determine that the end of the user's inhalation has been detected. Note that this threshold may be greater than, equal to, or smaller than the threshold in step 302. Alternatively, the control section 106 may determine that the end of the user's inhalation has been detected, based on a fact that a button for starting the generation of the aerosol has been released, etc.

When the end of the user's inhalation is not detected ("N" in step 312), the process returns to step 304.

When the end of the inhalation is detected by the user ("Y" in step 312), the process ends.

FIGS. 6A, 6B, 6C, and 6D show examples 600, 625, 650, and 675 of changes over time in an output value of a sensor and signals according to the processing 300 of FIG. 3, respectively. Reference numeral 602 shows an example of a change over a time t in an output value of the flow sensor or the like. Reference numerals 604 and 606 show examples of changes over the time t in signals transmitted to the switch Q1 and the switch Q2, respectively. Reference numeral 612 denotes a time point at which the output value of the flow sensor or the like exceeds the threshold and a time point at which the start of the inhalation has been detected in step 302, and reference numeral 614 denotes a time point at which the output value falls below the threshold. Note that in the present embodiment, a period 616 that starts at the time 612 and ends at time 614 is defined as a period during which the output value is generated by the above-described sensor. In addition, as described above, the above-described thresholds according to the times 612 and 614 may be the same as each other or one of the thresholds may be greater than the other. Reference numeral 618 denotes a time point at which the aerosol source is estimated to be insufficient in quantity in step 308. Reference numeral 620 denotes a period corresponding to a change in a signal made with one run of step 304, i.e., a switching period.

When the control section 106 controls the switches Q1 and Q2 according to the examples of the changes in signals shown in FIGS. 6A to 6D, the time period during which the switch Q1 is in an on state will be longer than the time period during which the switch Q2 is in an on state, in a period 616 during which the output value is generated by the above-described sensor. More specifically, when the control section 106 controls the switches Q1 and Q2 according to the examples of the changes in signals shown in FIG. 6A and FIG. 6B, the time period during which the switch Q1 is in an on state will be longer than the time period during which the switch Q2 is in an on state in one period 620. In addition, when the control section 106 controls the switches Q1 and Q2 according to the examples of the changes in signals shown in FIG. 6C, a plurality of time periods during which the switch Q2 is in an on state may occur with intervals in one period 620, but in such a case well, the time period during which the switch Q1 is in an on state will be longer than the sum of the time periods during which the switch Q2 is in an on state in one period 620. Furthermore, when the control section 106 controls the switches Q1 and Q2 according to the examples of the changes in signals shown in FIG. 6D, a plurality of time periods during which the switch Q1 is in an on state may occur with intervals in one period 620, but in such a case well, the sum of the time periods during which the switch Q1 is in an on state will be longer than the time period during which the switch Q2 is in an on state in one period 620. In this way, when the time period during which the switch Q1 is in an on state to generate the aerosol is longer than the time period during which the switch Q2 is in an on state to detect insufficiency of the aerosol source, the generation quantity of the aerosol is stabilized. It should be noted that in FIG. 6D, the time period during which the switch Q1 is in an on state occurs consecutively two times in one period 620, but it may occur consecutively three or more times.

It should be noted that the changes in signals shown in FIGS. 6A to 6D are merely examples. Hereinafter, some examples of a change in a signal made with one run of step 304 will be described with reference to FIGS. 7 to 12.

Figure 7:
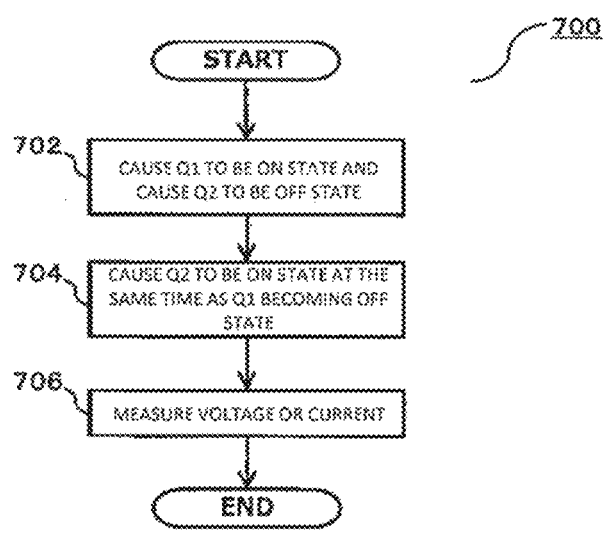
FIG. 7 is a flowchart of more specific exemplary processing included in the exemplary processing of determining whether an aerosol source is insufficient in quantity.

FIG. 7 is a flowchart of more specific first exemplary processing 700 that may be included in step 304.

Reference numeral 702 denotes a step in which the control section 106 causes the switch Q1 to be an on state and the switch Q2 to be an off state. In step 702, the control section 106 transmits an on signal and an off signal to the switches Q1 and Q2, respectively, so that the switches Q1 and Q2 become on states and off states, respectively. In step 702, the timing when the switch Q1 turns an on state and the timing when the switch Q2 turns an off state may be the same or whichever may come first. In addition, the transmission timing of the on signal to the switch Q1 and the transmission timing of the off signal to the switch Q2 may be the same or whichever may come first. Note that a main object of causing the switch Q1 to be an on state in step 702 is to generate the aerosol.

The process proceeds to step 704. In step 704, the control section 106 causes the switch Q2 to be an on state at the same time that the switch Q1 turns an off state. In step 702, the control section 106 transmits the off signal and the on signal to the switches Q1 and Q2, respectively, so that at the same time that the switch Q1 turns an off state, the switch Q2 turns an on state.

Figure 8:
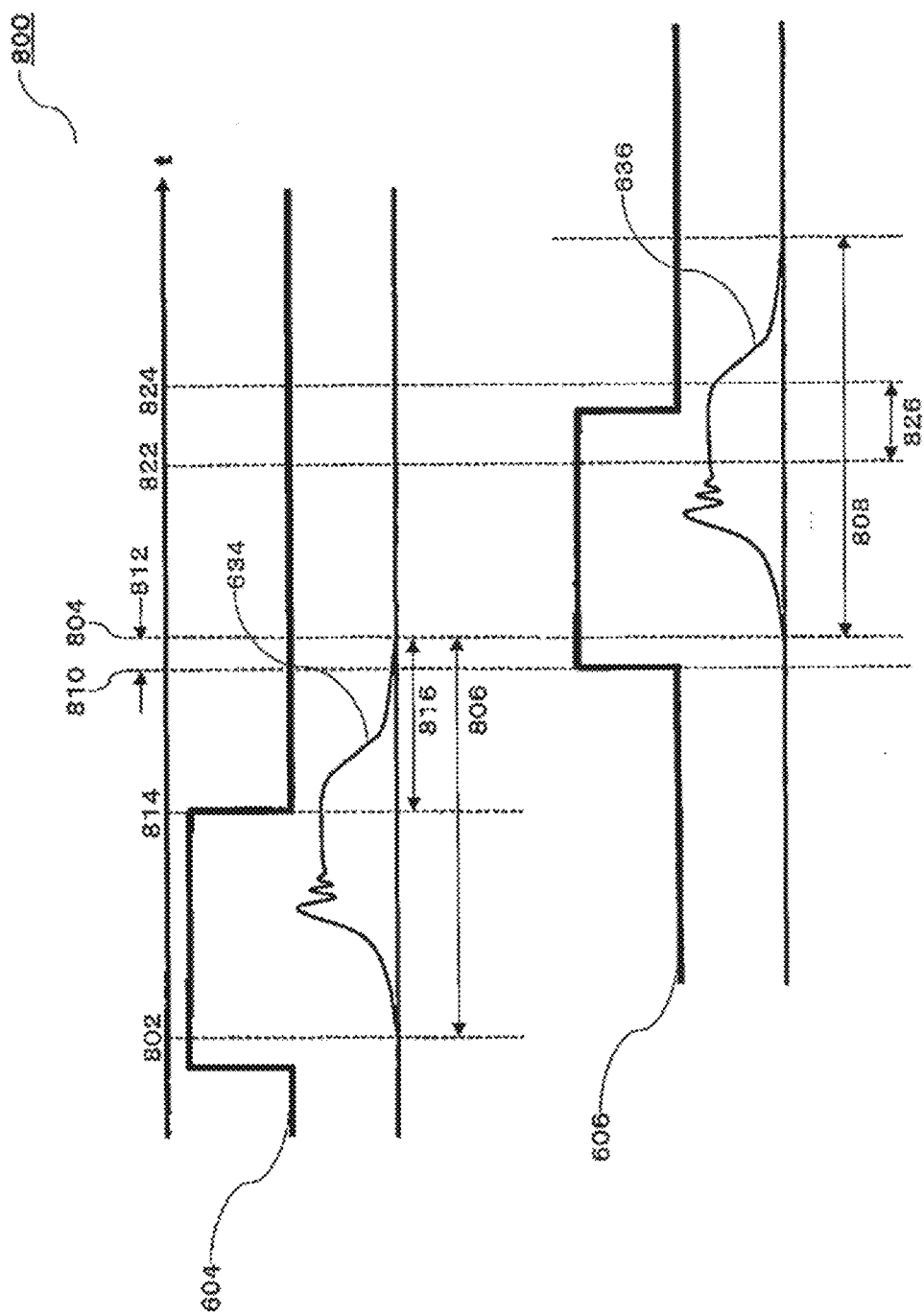
FIG. 8 is a graph showing a more detailed example of changes over time in signals according to the exemplary processing of determining whether an aerosol source is insufficient in quantity.

Here, an example 800 of changes over time in signals according to the first exemplary processing 700 will be described with reference to FIG. 8. Reference numerals 634 and 636 show examples of changes in the currents $I_{DS}$ of the first FET 206 and the second FET 210, respectively. Reference numerals 802 and 804 denote start and end time points of a period 806 during which the switch Q1 is in an on state, respectively. In the example 800 of the changes, the time 804 is also a time point at which a period 808 during which the switch Q2 is in an on state starts. Reference numeral 810 denotes a time point at which the on signal is transmitted to the switch Q2, and reference numeral 812 denotes a period between the time 810 and the time 804. FIG. 8 shows that the off signal is transmitted to the switch Q1 at the time 814 and the on signal is transmitted to the switch Q2 at the time 810 such that at the time 804, at the same time that the switch Q1 turns an off state, the switch Q2 turns an on state. Here, the turn-off time period (a length of a period 816) of the switch Q1 and a time period (a length of a period 812) from when the on signal is transmitted to the switch Q2 until the switch Q2 turns an on state have a predetermined length defined by the characteristics of the first FET 206 and the second FET 210 (and a circuit including paths from the control section 106 to the first FET 206 and the second FET 210). Accordingly, the control section 106 can obtain the time 810 by adding, to the time 814, a time period obtained by subtracting a length of the period 812 from the turn-off time period of the switch Q1.

Note that the control section 106 may transmit the on signal to the switch Q2 in the turn-off period (the period 816) of the switch Q1, more preferably, in the period from the time 814 to the time 810. Furthermore, the control section 106 may transmit the on signal to the switch Q2 in the period 806 during which the switch Q1 is in an on state, more preferably, in the period from the time 802 to the time 810. In other words, the control section 106 may transmit the on signal to the switch Q2 in a period that is included in the period 806 during which the switch Q1 is in an on state, the period ending before the time 804 when the period during which the switch Q1 is in an on state ends by the time period (the length of the period 812) being from when the on signal is transmitted to the switch Q2 until the switch Q2 turns an on state. When the on signal is transmitted to the switch at such a timing, the time period during which the load 132 is not energized or the time period during which a battery as the power supply 110 does not discharge is reduced (in other words, a rapid change in a discharge rate is suppressed), whereby the variation in the generation quantity of the aerosol and the deterioration of the battery can be suppressed.

Returning to FIG. 7, the process proceeds to step 706. In step 706, the control section 106 measures the voltage or the current. Here, referring again to FIG. 8, the measurement timing of the voltage or the current will be described. Reference numeral 822 denotes a time point (the time t7 in FIG. 4) when a current surge or a transient current fluctuation of the current $I_{DS}$ of the second FET 210 is settled, reference numeral 824 denotes a time point (the time t10 in FIG. 4) when the current $I_{DS}$ falls below a predetermined value, and reference numeral 826 denotes a period between these time points. It is preferable that the control section 106 measures the voltage or the current in the period 808 after the time 814 when the off signal is transmitted to the switch Q1, more preferably, in the period 826.

Figure 9:
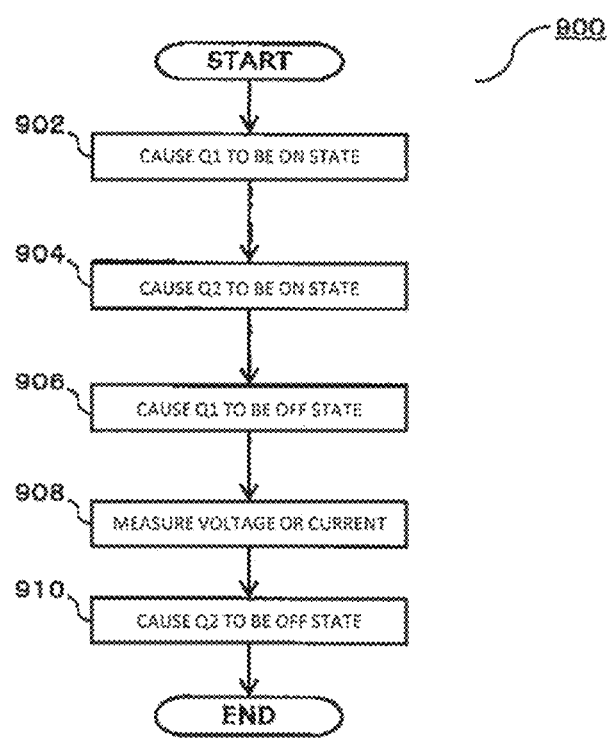
FIG. 9 is a flowchart of more specific exemplary processing included in the exemplary processing of determining whether an aerosol source is insufficient in quantity.

FIG. 9 is a flowchart of more specific second exemplary processing 900 that may be included in step 304. Reference numeral 902 denotes a step in which the control section 106 causes the switch Q1 to be an on state, reference numeral 904 denotes a step in which the control section 106 causes the switch Q2 to be an on state, and reference numeral 906 denotes a step in which the control section 106 causes the switch Q1 to be an off state. The control section 106 transmits the on signal and the off signal to the switch Q1 and transmits the on signal to the switch Q2, so that the switch Q1 turns an on state in step 902, the switch Q2 turns an on state in step 904, and the switch Q1 turns an off state in step 906.

Here, an example 1000 of changes overtime in signals according to the second exemplary processing 900 will be described with reference to FIG. 10. Reference numeral 1002 denotes a time point at which the off signal is transmitted to the switch Q1. In the example 1000 of the changes, the time 1002 is also a time point at which the off signal is transmitted to the switch Q2. Reference numeral 1004 denotes a time point at which a period 1006 during which the switch Q2 is in an on state starts, and reference numeral 1008 denotes a time point at which a period 1010 during which the switch Q1 is in an on state ends. In the example 1000 of the changes, the length of a period 1012 of the turn-off period of the switch Q1 is longer than the length of a period 1014 between the time 1002 and the time 1004.

Figure 10:
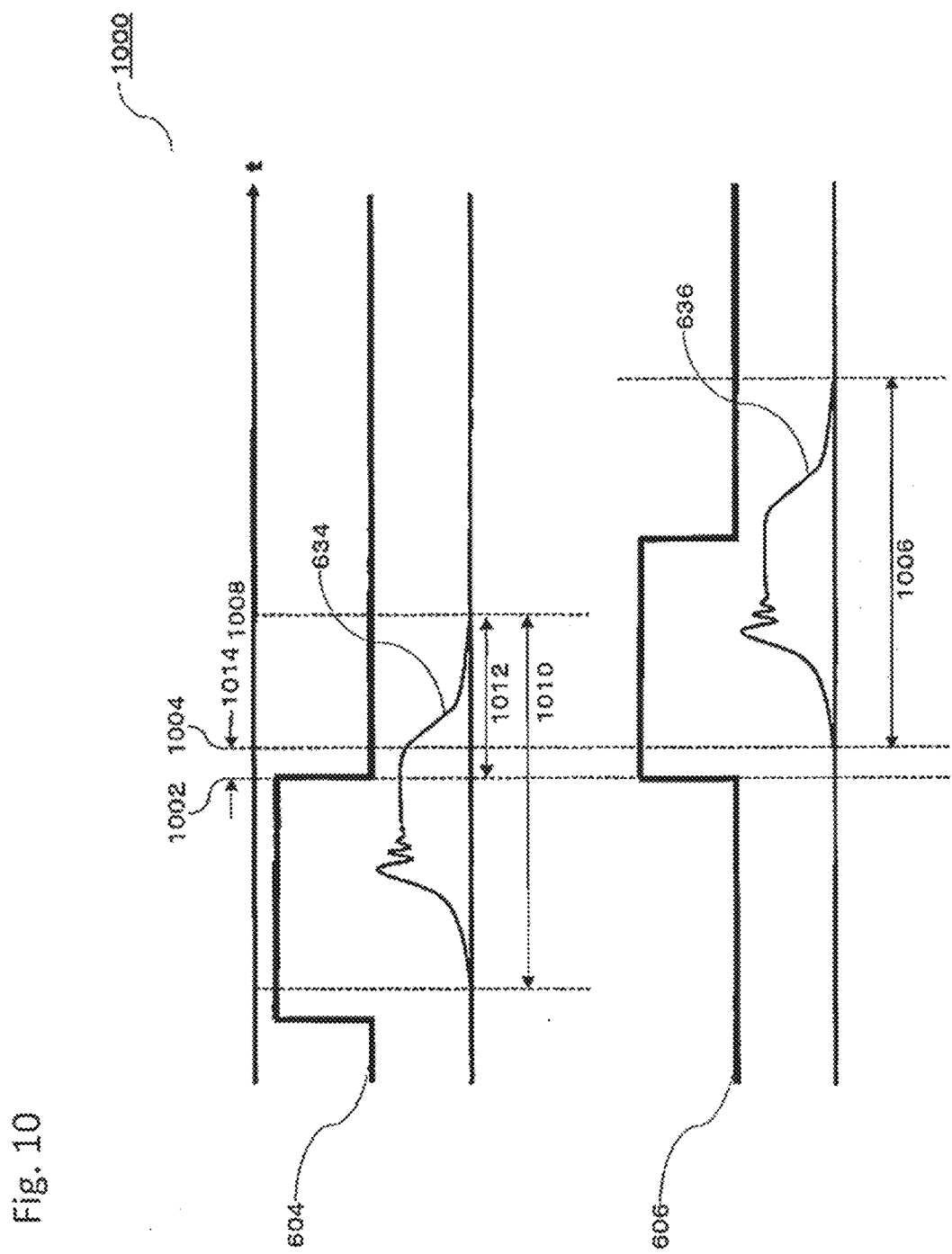
FIG. 10 is a graph showing a more detailed example of changes over time in signals according to the exemplary processing of determining whether an aerosol source is insufficient in quantity.

FIG. 10 shows that at the time 1002, at the same time that the off signal is transmitted to the switch Q1, the on signal is transmitted to the switch Q2, such that the switch Q2 turns an on state at the time 1004 before the time 1008 when the switch Q1 turns an off state, that is, when the switch Q1 is in an on state. It should be noted that when the length of the period 1012 is equal to or longer than the length of the period 1014, that is, the turn-off time period of the switch Q1 is equal to or longer than a time period from when the on signal is transmitted to the switch Q2 until the switch Q2 turns an on state by transmitting the off signal to the switch Q1 while simultaneously transmitting the on signal to the switch Q2, the switch Q2 turns an on state when the switch Q1 is in an on state or the switch Q2 turns an on state at the same that the switch Q1 turns an off state. When the off signal and the on signal are thus simultaneously transmitted, the time period during which the load 132 is not energized or the time period during which a battery as the power supply 110 does not discharge is reduced, whereby the variation in the generation quantity of the aerosol and the deterioration of the battery can be simultaneously suppressed. In addition, FIG. 10 also shows that the on signal is transmitted to the switch Q2 when the switch Q1 is in an on state. Note that the control section 106 may transmit the on signal to the switch Q2 before or after the time point when the control section 106 transmits the off signal to the switch Q1, so that the switch Q2 turns anon state when the switch Q1 is in anon state. In this way, when the on signal is transmitted to one of the switches while the other switch is in an on state, the time period during which the load 132 is not energized or the time period during which a battery as the power supply 110 does not discharge is reduced, whereby the variation in the generation quantity of the aerosol and the deterioration of the battery can be simultaneously suppressed.

Returning to FIG. 9, the process proceeds to step 980. In step 908, the control section 106 measures the voltage or the current. The control section 106 can measure the voltage or the current at a similar timing to that described above with respect to FIG. 8.

The process proceeds to step 910. In step 910, the control section 106 causes the switch Q2 to become an off state. The control section 106 can transmit the off signal to the switch Q2 so that the switch Q2 turns an off state in step 910.

Figure 11:
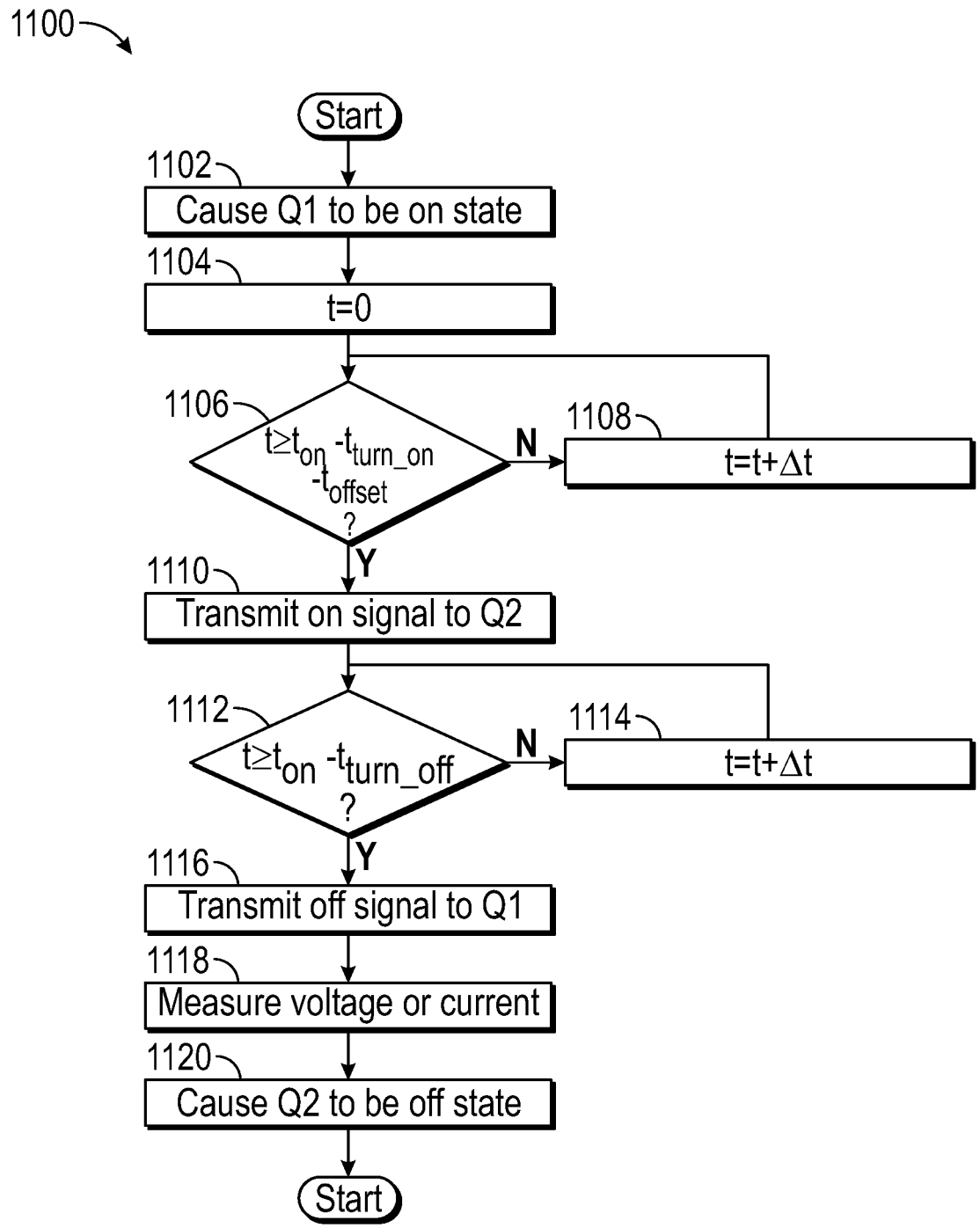
FIG. 11 is a flowchart of more specific exemplary processing included in the exemplary processing of determining whether an aerosol source is insufficient in quantity.

FIG. 11 is a flowchart of more specific third exemplary processing 1100 that may be included in step 304.

Reference numeral 1102 denotes a step in which the control section 106 causes the switch Q1 to be an on state. In step 1102, the control section 106 transmits the on signal to the switch Q1 so that the switch Q1 turns an on state.

Reference numeral 1104 denotes a step in which the control section 106 initializes, to zero, a variable t for controlling the timing when the off signal is transmitted to the switch Q1 and the timing when the on signal is transmitted to the switch Q2 in the exemplary processing 1100.

The process proceeds to step 1106. In step 1106, the control section 106 determines whether the variable t is equal to or larger than a value obtained by subtracting, from the time period $t_{on}$ during which the switch Q1 is in an on state, the turn-on time period $t_{turn\_on}$ of the switch Q2 and an offset time period $t_{offset}$. The offset time period $t_{offset}$ can be an arbitrary value that satisfies $0 \leq t_{offset} < t_{on} - t_{turn\_off}$.

When it is not determined that the variable t is equal to or larger than $t_{on} - t_{turn\_on} - t_{offset}$ ("N" in step 1106), the process proceeds to step 1108, and in step 1108, the control section 106 adds Δt to the variable t, and the process returns to step 1106. It should be noted that step 1108 may be repeated a plurality of times before the process proceeds to step 1110. A value of Δt in step 1108 is a value indicating a time period having elapsed since a time point at which step 1108 was performed lastly (a time point at which step 1104 was performed in the case where step 1108 was first performed).

When it is determined that the variable t is equal to or larger than $t_{on} - t_{turn\_on} - t_{offset}$ ("Y" in step 1106), the process proceeds to step 1110. In step 1110, the control section 106 transmits the on signal to the switch Q2.

The process proceeds to step 1112. In step 1112, the control section 106 determines whether the variable t is equal to or larger than a value obtained by subtracting, from the time period $t_{on}$ during which the switch Q1 is in an on state, the turn-off time period $t_{turn\_off}$ of the switch Q1.

When it is not determined that the variable t is equal to or larger than $t_{on} - t_{turn\_off}$ ("N" in step 1112), the process proceeds to step 1114. In step 1114, the control section 106 adds Δt to the variable t, and the process returns to step 1112. It should be noted that step 1114 may be repeated a plurality of times before the process proceeds to step 1116. A value of Δt in step 1114 is a value indicating a time period having elapsed since a time point at which step 1114 was performed lastly (a time point at which step 1108 was performed lastly in the case where step 1114 was first performed (a time point at which step 1104 was performed if step 1108 was never performed)).

When it is determined that the variable t is equal to or larger than $t_{on} - t_{turn\_off}$ ("Y" in step 1112), the process proceeds to step 1116. In step 1116, the control section 106 transmits the off signal to the switch Q1.

Here, an example 1200 of changes overtime in signals according to the third exemplary processing 1100 will be described with reference to FIG. 12. Reference numerals 1202 and 1204 denote start and end time points of a period 1206 during which the switch Q1 is in an on state, respectively. In the example 1200 of the changes, the time 1204 is also a time point at which a period 1208 that is the turn-on period of the switch Q2 ends. Reference numeral 1210 denotes a time point at which the on signal is transmitted to the switch Q2, and the period 1208 that is the turn-on period of the switch Q2 starts. Reference numeral 1212 denotes a time point at which the off signal is transmitted to the switch Q1, and therefore, reference numeral 1214 denotes a period of the turn-off period of the switch Q1. Furthermore, reference numeral 1216 denotes a period of the turn-on period of the switch Q1, and reference numeral 1218 denotes a period during which the switch Q2 is in an on state.

Figure 12:
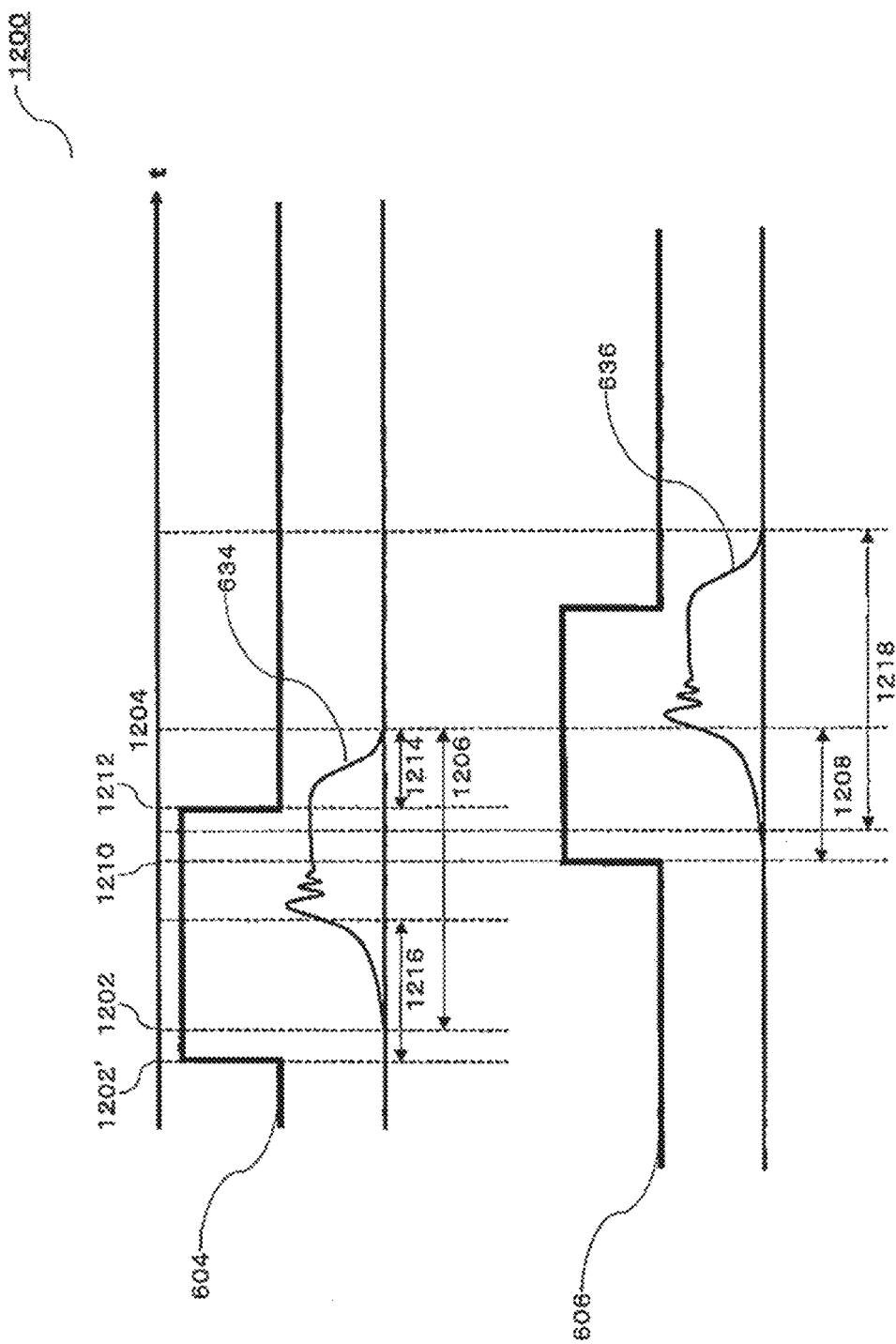
FIG. 12 is a graph showing a more detailed example of changes over time in signals according to the exemplary processing of determining whether an aerosol source is insufficient in quantity.

FIG. 12 shows that the off signal is transmitted to the switch Q1 at the time 1212 after the on signal is transmitted to the switch Q2 at the time 1210. In this way, when the off signal is transmitted to one of the switches after the on signal is transmitted to the other switch, the current flowing through the switch that turns an on state can be stabilized. In addition, FIG. 12 also shows that the time 1210 is a time point at which a time period has elapsed since the time 1202, the time period being obtained by subtracting the turn-on time period $t_{turn\_on}$ of the switch Q2 (a length of the period 1208) from the time period $t_{on}$ (a length of the period 1206) during which the switch Q1 is in an on state. It will be appreciated that when the control section 106 is configured to perform step 1104 immediately after step 1102, set $t_{offset}$ in step 1106 to zero, sufficiently reduce Δt in step 1108, and then perform step 1110 immediately after determination in step 1106, the control section 106 can transmit the on signal to the switch Q2 at the time 1210 by the third exemplary processing 1100. Furthermore, it will be appreciated that by setting $t_{offset}$ to an appropriate value, the control section 106 can transmit the on signal to the switch Q2 at an arbitrary timing between the time 1202 and the time 1210, in other words, before the elapse of a time period since a time point at which the switch Q1 turns an on state, the time period being obtained by subtracting, from the time period during which the switch Q2 is in an on state, the turn-on time period of the switch Q2. Accordingly, the control section 106 can also transmit the on signal to the switch Q2 in the period 1216 that is the turn-on period of the switch Q1. In this way, when, before the remainder of the period during which one of the switches is in an on state becomes shorter than the turn-on time period of the other switch, the control section 106 transmits the on signal to the other switch, the time period during which the load 132 is not energized or the time period during which a battery as the power supply 110 does not discharge is reduced, whereby the variation in the generation quantity of the aerosol and the deterioration of the battery can be simultaneously suppressed. Note that the control section 106 may control the transmission timing of the on signal to the switch Q2 by replacing the above-described time 1202 with a time 1202' when the on signal is transmitted to the switch Q1.

In addition, FIG. 12 shows that the time 1212 is a time point at which a time period has elapsed since the time 1202, the time period obtained by subtracting, from the time period $t_{on}$ (a length of the period 1206) during which the switch Q1 is in an on state, the turn-off time period $t_{turn\_off}$ (a length of the period 1214) of the switch Q1. It will be appreciated that when the control section 106 is configured to sufficiently reduce Δt in step 1114, and perform step 1116 immediately after determination in step 1112, the control section 106 can transmit the off signal to the switch Q1 at the time 1212 by the third exemplary processing 1100.

Returning to FIG. 11, the process proceeds to step 1118. In step 1118, the control section 106 measures the voltage or the current. Here, referring again to FIG. 12, the measurement timing of the voltage or the current will be described.

The control section 106 can measure the voltage or the current at the time 1212 when the off signal is transmitted to the switch Q1. In addition, the control section 106 can measure the voltage or the current after the time 1212 when the off signal is transmitted to the switch Q1 and in the period 1218 during which the switch Q2 is in an on state. In this way, when, after the off signal is transmitted to one of the switches, the control section 106 measures the voltage or the current, and e.g., calculates the resistance value, the current flowing through the other switch is easily stabilized, whereby the estimation accuracy of a residual quantity of the aerosol source is improved. More preferably, the control section 106 can measure the voltage or the current at the time 1204 and thereafter that is after the elapse of the turn-off time period (a length of the period 1214) of the switch Q1 since the time 1112 when the off signal is transmitted to the switch Q1 and in the period 1218 during which the switch Q2 is in an on state. In this way, when, after one of the switches turns an off state, the control section 106 measures the voltage or the current, and e.g., calculates the resistance value, the current flowing through the other switch is more easily stabilized, whereby the estimation accuracy of a residual quantity of the aerosol source is further improved.

In addition, when the control section 106 measures the voltage or the current at the time 1212 when the off signal is transmitted to the switch Q1 or immediately thereafter, at the measurement time point, the switch Q1 is still in an on state and the aerosol source is generated in principle. Exceptionally, even when the aerosol source is insufficient in quantity, it is not estimated that the aerosol source is insufficient in quantity, in step 308 in FIG. 3 that is performed immediately before step 1118 (included in step 304 in FIG. 3) of measuring the voltage or the current, and therefore the measurement time point is immediately after the generation of the aerosol source is stopped. The measurement time point is in the period 1218 during which the switch Q2 is in an on state and in the period 616 during which the output value is generated by the pressure sensor, the flow sensor or the like. Accordingly, according to the third exemplary processing 1100, the control section 106 measures the voltage or the current when the switch Q2 is in an on state, when the output is generated by the above-described sensor, and when the aerosol is generated by the load 132, or immediately after the generation of the aerosol by the load 132 is stopped, whereby the control section 106 can perform step 308 of estimating the residual quantity of the aerosol source.

Returning again to FIG. 11, the process proceeds to step 1120. In step 1120, the control section 106 causes the switch Q2 to become an off state. The control section 106 transmits the off signal to the switch Q2 so that the switch Q2 turns an off state in step 1120.

FIGS. 8, 10, and 12 show examples 800, 1000, and 1200 of the changes in signals of the switches Q1 and Q2, respectively, for causing the switch Q2 to be an on state when the switch Q1 is in an on state or causing the switch Q1 to be an off state while simultaneously causing the switch Q2 to be an on state. Here, the control section 106 may transmit the on signal and the off signal to the switches Q1 and Q2 so that the switch Q1 turns an on state when the switch Q2 is in an on state or the switch Q2 turns an on state at the same time that the switch Q2 turns an off state. The changes in signals of the switches Q1 and Q2 for doing so correspond to a case where the switches Q1 and Q2 are transposed in the above description.

Furthermore, in the period 616 (see FIGS. 6A to 6D) during which the output is generated by the sensor such as the pressure sensor and the flow sensor except the period after the time 618 when it is estimated that the aerosol source is insufficient in quantity, at least one of the switch Q1 and the switch Q2 is in an on state, in the case where the switch Q2 turns an on state when the switch Q1 is in an on state or the switch Q2 turns an on state at the same time that the switch Q1 turns an off state and in the case where the switch Q1 turns an on state when the switch Q2 is in an on state or the switch Q1 turns an on state at the same time that the switch Q2 turns an off state. Accordingly, the power supply by the power supply 110, particularly, the power supply to the load 132 continues. In other words, in principle, that is, except the case where the aerosol source is exceptionally insufficient in quantity, the control section 106 can be configured to control the switch Q1 and the switch Q2 so that the power supply by the power supply 110 continues while the output is generated by the sensor. According to the above configuration, at least one of the switch Q1 for generating the aerosol and the switch Q2 for detecting the insufficiency of the aerosol source is in an on state during the inhalation, whereby the variation in the generation quantity of the aerosol and the deterioration of the battery as the power supply 110 can be simultaneously suppressed even when the residual quantity of the aerosol source is estimated during the inhalation.

Figure 13:
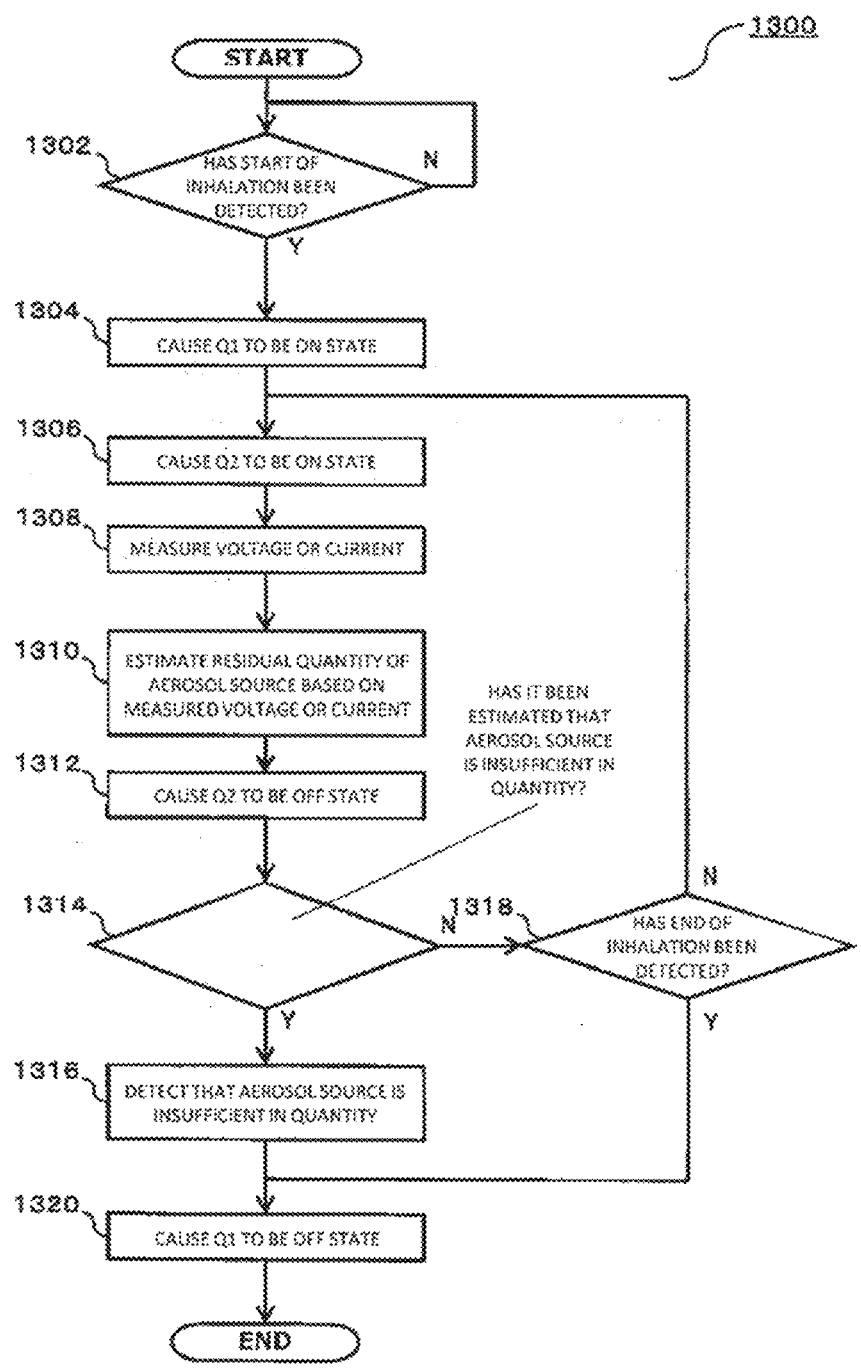
FIG. 13 is a flowchart of exemplary processing of determining whether an aerosol source is insufficient in quantity, according to an embodiment of the present disclosure.

FIG. 13 is a flowchart of exemplary processing 1300 of determining whether the aerosol source is insufficient in quantity, according to an embodiment of the present disclosure. Here, all the steps will be described as being performed by the control section 106. However, it should be noted that some of the steps may be performed by another component in the aerosol generation apparatus 100.

The process starts at step 1302. Step 1302 is a step similar to step 302 of FIG. 3.

When it is determined that the start of the inhalation has been detected ("Y" in step 1302), the process proceeds to step 1304. In step 1304, the control section 106 causes the switch Q1 to be an on state. The control section 106 transmits the on signal to the switch Q1 so that the switch Q1 turns an on state in step 1304.

The process proceeds to step 1306. In step 1306, the control section 106 causes the switch Q2 to be an on state. The control section 106 transmits the on signal to the switch Q2 so that the switch Q2 turns an on state in step 1306.

The process proceeds, subsequent to step 1308, to step 1310. Step 1308 is a step similar to step 706 in FIG. 7, step 908 in FIG. 9, and step 1118 in FIG. 11, and step 1310 is a step similar to step 306 in FIG. 3.

The process proceeds to step 1312. In step 1312, the control section 106 causes the switch Q2 to become an off state. The control section 106 transmits the off signal to the switch Q2 so that the switch Q2 turns an off state in step 1312.

The process proceeds, subsequent to step 1314, to step 1316 or 1318. Steps 1314, 1316, and 1318 are steps similar to steps 308, 310, and 312 in FIG. 3, respectively.

Reference numeral 1320 denotes a step in which the control section 106 causes the switch Q1 to become an off state. The control section 106 transmits the off signal to the switch Q1 so that the switch Q1 turns an off state in step 1320.

Figure 14:
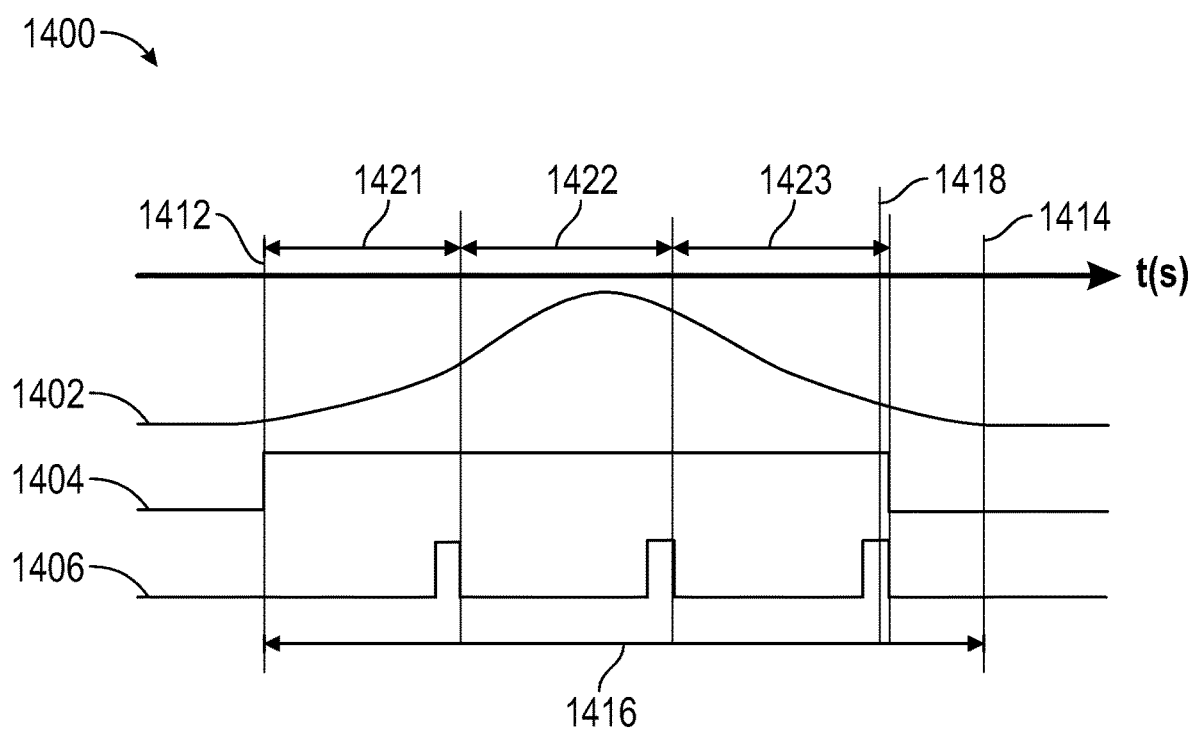
FIG. 14 is a graph showing an example of changes over time in an output value of a sensor and signals according to the exemplary processing of determining whether an aerosol source is insufficient in quantity.

FIG. 14 shows an example 1400 of changes over the time in the output value of the sensor and the signals, according to the processing 1300 of FIG. 13. Reference numerals 1402, 1404, 1406, 1412, 1414, and 1416 are the same as reference numerals 602, 604, 606, 612, 614, and 616 in FIGS. 6A to 6D, respectively. Reference numeral 1418 denotes a time point at which it is estimated that the aerosol source is insufficient in quantity in step 1316. Reference numeral 1421 denotes a period corresponding to changes in signals at least while processes from step 1304 to step 1312 are performed one time, reference numeral 1422 denotes a period corresponding to changes in signals at least while processes from step 1306 to step 1312 are performed one time, and reference numeral 1423 denotes a period corresponding to changes in signals at least while processes from step 1306 to step 1320 are performed one time.

FIG. 14 shows that in the period 1416 during which the output is generated by the sensor such as the pressure sensor and the flow sensor except the period after the time 1418 when it is estimated that the aerosol source is insufficient in quantity, the switch Q1 is always in an on state and the switch Q2 is intermittently in an on state, that is, the power supply by the power supply 110 continues. In other words, according to the exemplary processing 1300, in principle, that is, except the case where the aerosol source is exceptionally insufficient in quantity, the control section 106 is configured to cause the switch Q1 to be always an on state and the switch Q2 to be intermittently an on state while the output is generated by the sensor. According to the above configuration, the time period during which the load 132 is not energized or the time period during which a battery as the power supply 110 does not discharge is reduced, whereby the variation in the generation quantity of the aerosol and the deterioration of the battery can be suppressed. In particular, when the electric resistance value of the resistor 212 is sufficiently higher than the electric resistance value of the load 132, a change in a discharge rate of the power supply 110 due to the intermittent turning on of the switch Q2 is small enough to be negligible. Accordingly, in the period 1416 during which the output is generated by the sensor such as the flow sensor except the period after the time 1418 when it is estimated that the aerosol source is insufficient in quantity, the discharge rate of the power supply 110 is substantially constant, whereby the deterioration of the battery as the power supply 110 can be effectively suppressed.

In the above description, the embodiments of the present disclosure have been described as an aerosol generation apparatus and a method of operating the aerosol generation apparatus. However, it will be appreciated that the present disclosure, when being executed by a processor, can be implemented as a program that causes the processor to perform the method or as a computer readable storage medium storing the same program.

The embodiments of the present disclosure have been described thus far, and it should be understood that these embodiments are only illustration, and do not limit the scope of the present disclosure. It should be understood that modification, addition, alteration and the like of the embodiments can be properly performed without departing from the spirit and the scope of the present disclosure. The scope of the present disclosure should not be limited by any of the aforementioned embodiments, but should be specified by only the claims and the equivalents of the claims.

REFERENCE SIGNS LIST 100A, 100 . . . aerosol generation apparatus, 102 . . . main body, 104A . . . cartridge, 104B aerosol generating article, 106 . . . control section, 108 . . . notifying section, 110 . . . power supply, 112A to 112D . . . sensor, 114 . . . memory, 116A . . . storage section, 116B . . . aerosol base material, 118A, 118B . . . atomizing section, 120 . . . air intake channel, 121 . . . aerosol flow path, 122 . . . mouthpiece section, 130 . . . retention section, 132 . . . load, 134 . . . circuit, 202 . . . first circuit, 204 . . . second circuit, 206, 210, 214 . . . FET, 208 . . . conversion section, 212 . . . resistor, 216 . . . diode, 218 . . . inductor, 220 . . . capacitor, 402 . . . signal to switch, 404 voltage between gate and source of FET included in switch, 406 . . . current flowing between drain and source of FET included in switch, 502 . . . quantity of aerosol source retained in retention section 130, 512 . . . temperature of load, 514 . . . resistance value of load, 602, 1402 . . . output value of sensor, 604, 1404 . . . signal to switch Q1, 606, 1406 . . . signal to switch Q2, 634 . . . current flowing between drain and source of FET included in switch Q1, 636 . . . current flowing between drain and source of FET included in switch Q

The invention claimed is:

1. An aerosol generation apparatus, comprising:
   a container configured to store an aerosol source or an aerosol base material that retains the aerosol source;
   a first sensor configured to generate an output upon receipt of a user's request with regard to an aerosol generation;
   a first circuit connected in series between a power supply and a load, wherein the first circuit includes a first switch;
   a second circuit connected in parallel with the first circuit to the power supply and the load, wherein the second circuit includes a second switch and has an electric resistance value higher than an electric resistance value of the first circuit; and
   processing circuitry configured to
   control the aerosol generation apparatus so that a period during which the output is generated by the first sensor includes:
      a time point at which the second switch turns to an on state when the first switch is in an on state, or
      a time point at which the second switch turns to an on state at the same time as the first switch becoming an off state.

2. The aerosol generation apparatus according to claim 1, wherein the processing circuitry is further configured to:
   cause the second switch to be in an on state after the first switch turns to an on state; and
   simultaneously transmit an off signal to the first switch and an on signal to the second switch.

3. The aerosol generation apparatus according to claim 1, wherein the processing circuitry is further configured to:
   cause the first switch to be in an on state after the second switch turns to an on state; and
   simultaneously transmit an on signal to the first switch and an off signal to the second switch.

4. The aerosol generation apparatus according to claim 1, wherein the processing circuitry is further configured to
   transmit, when one of the first switch and the second switch is in an on state, an on signal to the other of the first switch and the second switch.

5. The aerosol generation apparatus according to claim 4, wherein the processing circuitry is further is configured to:
   maintain an on state of the first switch for a predetermined time period; and
   transmit an on signal to the second switch before an elapse of a time period since an on signal is transmitted to the first switch or the first switch turns to an on state, the time period being obtained by subtracting, from the predetermined time period, a turn-on time period of the second switch.

6. The aerosol generation apparatus according to claim 4, wherein the processing circuitry is further configured to
   transmit an off signal to the one of the first switch and the second switch after an on signal is transmitted to the other of the first switch and the second switch.

7. The aerosol generation apparatus according to claim 1, wherein the processing circuitry is further configured to
   transmit, during a turn-off period of one of the first switch and the second switch, an on signal to the other of the first switch and the second switch.

8. The aerosol generation apparatus according to claim 1, wherein the processing circuitry is further configured to
   transmit, during a turn-on period of one of the first switch and the second switch, an off signal to the other of the first switch and the second switch.

9. The aerosol generation apparatus according to claim 1, wherein the processing circuitry is further configured to
   estimate a residual quantity of the aerosol source based on a value output by a second sensor after an off signal is transmitted to the first switch, wherein the second sensor is configured to output a value related to an electric resistance value of a load, wherein an electric resistance value changes depending on a temperature of the load, which atomizes the aerosol source using heat generated by electric power from the power supply.

10. The aerosol generation apparatus according to claim 1, wherein the processing circuitry is further configured to
    estimate a residual quantity of the aerosol source based on a value output by a second sensor after an elapse of a turn-off time period of the first switch since transmission of an off signal to the first switch, the second sensor is configured to output a value related to an electric resistance value of a load, wherein an electric resistance value changes depending on a temperature of the load, which atomizes the aerosol source using heat generated by electric power from the power supply.

11. The aerosol generation apparatus according to claim 1, wherein the processing circuitry is further configured to
    cause the first switch to be always in an on state and the second switch to be intermittently in an on state while the output is generated by the second sensor.

12. The aerosol generation apparatus according to claim 1, wherein the processing circuitry is further configured to
    cause a time period during which the first switch is in an on state to be longer than a time period during which the second switch is in an on state while the output is generated by the first sensor.

13. The aerosol generation apparatus according to claim 1, comprising
    a voltage converter connected between the power supply and a node, wherein the node is connected to a higher voltage side of the first circuit and a higher voltage side of the second circuit, wherein
    the processing circuitry is further configured to control the voltage converter to output a constant voltage while the second switch is in an on state.

14. The aerosol generation apparatus according to claim 1, wherein the first switch and the second switch are comprised of any of switches having the same characteristics, transistors having the same characteristics, and contactors having the same characteristics.

15. The aerosol generation apparatus according to claim 1, wherein the first sensor is configured to detect a flow rate or a flow velocity generated by a user's inhalation through the aerosol generation apparatus, and generate the output only while the flow rate or the flow velocity exceeds a first threshold and does not fall below a second threshold.

16. The aerosol generation apparatus according to claim 1, wherein the first sensor is configured to detect a change in a pressure generated by a user's inhalation through the aerosol generation apparatus, and generate the output only while the pressure falls below a first threshold and does not exceed a second threshold.

17. The aerosol generation apparatus according to claim 1, wherein
    a period during which a switch is in an on state is a period from when a current flowing through the switch becomes higher than a predetermined value until the current decreases to the predetermined value, and a period during which a switch is in an off state is a period during which the switch is not in an on state.

* * * * *